(12) United States Patent
Zhang et al.

(10) Patent No.: US 9,303,039 B2
(45) Date of Patent: Apr. 5, 2016

(54) METHODS USEFUL IN THE SYNTHESIS OF HALICHONDRIN B ANALOGS

(71) Applicant: Eisai R&D Management Co., Ltd., Tokyo (JP)

(72) Inventors: Huiming Zhang, Andover, MA (US); Bryan M. Lewis, North Brunswick, NJ (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/562,086

(22) Filed: Dec. 5, 2014

(65) Prior Publication Data

US 2015/0158881 A1    Jun. 11, 2015

Related U.S. Application Data

(60) Provisional application No. 61/912,714, filed on Dec. 6, 2013.

(51) Int. Cl.
*C07D 321/00* (2006.01)
*C07D 493/22* (2006.01)

(52) U.S. Cl.
CPC .................................. *C07D 493/22* (2013.01)

(58) Field of Classification Search
CPC .................................................... C07D 493/22
USPC ......................................................... 549/348
See application file for complete search history.

(56) References Cited

U.S. PATENT DOCUMENTS

| | | |
|---|---|---|
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 2007/0244187 A1 | 10/2007 | Austad et al. |
| 2009/0203771 A1 | 8/2009 | Inanaga et al. |
| 2014/0163244 A1 | 6/2014 | Hu |
| 2015/0175620 A1 | 6/2015 | Endo et al. |
| 2015/0225415 A1 | 8/2015 | Chase et al. |
| 2015/0232490 A1 | 8/2015 | Benayoud et al. |

FOREIGN PATENT DOCUMENTS

| | | |
|---|---|---|
| EP | 0572109 A1 | 12/1993 |
| JP | H06-211737 A | 8/1994 |
| WO | WO-93/17690 A1 | 9/1993 |
| WO | WO-2006/076100 A2 | 7/2006 |
| WO | WO-2009/064029 A1 | 5/2009 |
| WO | WO-2012/147900 A1 | 11/2012 |
| WO | WO-2015/066729 A1 | 5/2015 |

OTHER PUBLICATIONS

Austad et al. Synlett, 24(3), 333-337; 2013.*
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4 (1992).
Aicher, Thomas Daniel, Thesis, Chapter 4, "Synthetic studies towards halichondrin B," Doctor of Philosophy in Chemistry, Harvard University, 35-54 (1990).
Alley et al. "Comparison of the relative efficacies and toxicities of Halichondrin B analogues," Proceedings of the AACR-NCL-EORTC Conference on Molecular Targets and Cancer Therapeutics. C230:257 (2005).
Anderson, "Developing processes for crystallization-induced asymmetric transformation," Org Process Res Dev. 9:800-13 (2005).
Austad et al., "Commercial manufacture of Halaven®: chemoselective transformations en route to structurally complex macrocyclic ketones," Synlett. 24 (2013). Supporting Information, (13 pages.).
Austad et al., "Commercial manufacture of Halaven®: chemoselective transformations en route to structurally complex macrocyclic ketones," Synlett. 24:333-7 (2013).
Austad et al., "Process development of Halaven®: synthesis of the C14-C35 fragment via iterative Nozaki-Hiyama-Kishi reaction—Williamson ether cyclization," Synlett. 24:327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).
Bernet et al., "Carbocyclische verbindungen aus monosacchariden. Umsetzungen in der glucosereihe," Hely Chim Acta. 62(6):1990-2016 (1979).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20) → C(36) precursor," Tetrahedron Lett. 36(39):7023-6 (1995).
Burke et al., "Synthesis of a C(22)-C(34) Halichondrin B precursor via ring opening—double ring closing metathesis," J Org Chem. 63:8626-7 (1998).
Burke et al., "Synthesis of a C(22) → C(34) Halichondrin precursor via a double dioxanone-to-dihydropyran rearrangement," Tetrahedron Lett. 32(32):3961-4 (1991).

(Continued)

*Primary Examiner* — Nizal Chandrakumar
(74) *Attorney, Agent, or Firm* — Clark & Elbing LLP

(57) ABSTRACT

In general, the present invention features improved methods useful for the synthesis of analogs of halichondrin B, such as eribulin and pharmaceutically acceptable salts thereof (e.g., eribulin mesylate).

12 Claims, No Drawings

(56) References Cited

OTHER PUBLICATIONS

Burke et al., "Synthetic studies toward complex polyether macrolides of marine origin," Spec Publ R Soc Chem. 198:(Anti-Infectives) 73-85 (1997).
Carruthers et al. *Modern Methods of Organic Synthesis, Fourth Edition*. Cambridge University Press, 65 (2004).
Chase et al., "Process development of Halaven®: Synthesis of the C1-C13 fragment from D-(-)-Gulono-1, 4-lactone," Synlett. 24(3):323-6 (2013).
Chen et al., "Ni(II)/Cr(II)-mediated coupling reaction: An asymmetric process," J Org Chem. 60(17):5386-7 (1995).
Choi et al., "Assymetric Ni(II)/Cr(II)-mediated coupling reaction: catalytic process," Org Lett. 4(25):4435-8 (2002).
Choi et al., "Synthetic studies on the marine natural product Halichondrins," Pure Appl Chem. 75(1):1-17 (2003).
Cooper et al., "Total Synthesis of Halichondrin B from common sugars: an F-ring intermediate from D-glucose and efficient construction of the C1 to C21 segment," Tetrahedron Lett. 34(51):8193-6 (1993).
Cunningham et al., "The influence of pH on the kinetic constants of alpha-chymotrypsin-catalyzed esterolysis," J Biol Chem. 221(1):287-300 (1956).
Dabydeen et al. "Comparison of the activities of the truncated Halichondrin B analog NSC 707389 (E7389) with those of the parent compound and a proposed binding site on tubulin," Mol Pharmacol. 70(6):1866-75 (2006).
Dong et al. "New syntheses of E7389 C14-C35 and halichondrin C14-C38 building blocks: reductive cyclization and oxy-michael cyclization approaches," J Am Chem Soc. 131(43):15642-6 (2009).
Duan et al., "Synthetic studies on halichondrins: a new practical synthesis of the C.1-C.12 segment," Tetrahedron Lett. 34(47):7541-4 (1993).
Flemming et al., "Nitrile anion cyclizations," Tetrahedron. 58(1):1-23 (2002).
Greene et al. *Protective Groups in Organic Synthesis, Third Edition*. John Wiley & Sons, Inc., 24, 127, 128, 134, 142, 170, 207, 209, 215, and 216 (1999).
Greene et al., *Protective Groups in Organic Synthesis, Third Edition*. John Wiley & Sons, Inc., 133-9 (1999).
Guo et al., "Toolbox approach to the search for effective ligands for catalytic asymmetric Cr-mediated coupling reactions," J Am Chem Soc. 131(42):15387-93 (2009).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B.," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed Lewis acids," Chem Pharm. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide issolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
International Search Report and Written Opinion for International Application No. PCT/US14/68834, mailed Mar. 3, 2015 (17 pages).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al. "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kim et al., "New syntheses of E7389 C14-C35 and Halichondrin C14-C38 building blocks: double-inversion approach," J Am Chem Soc. 131(43):15636-41 (2009).
Kurosu et al., "Fe/Cr- and Co/Cr-mediated catalytic asymmetric 2-Haloallylations of aldehydes," J Am Chem Soc. 126(39):12248-9 (2004).
March. *Advanced Organic Chemistry, Fourth Edition*. John Wiley and Sons, 348-357 (1992).
March. *Advanced Organic Chemistry, Fourth Edition*. John Wiley & Sons, 386-388 (1992).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).
Nicolaou et al., "Total synthesis of the CP molecules CP-263,114 and CP-225,917—Part 1: synthesis of key intermediates and intelligence gathering," Angew Chem Int Ed. 38(11):1669-75 (1999).
Ritter, "Synthetic transformations of vinyl and aryl triflates," Synthesis: Reviews. 8:735-62 (1993).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al. "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48): 8647-50 (1996).
Stamos et al., "New synthetic route to the C.14-C.38 segment of Halichondrins," J Org Chem. 62(22):7552-3 (1997).
Stamos et al., "Synthetic studies on Halichondrins: a practical synthesis of the C.1-C.13 segment," Tetrahedron Lett. 37(48):8643-6 (1996).
Stamos, et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Sutherland et al., "The synthesis of 6alpha- and 6beta-fluoroshikimic acids," J Chem Soc Chem Commun. 18:1386-7 (1989).
Takai et al. "Reactions of alkenylchromium reagents prepared from alkenyl trifluoromethanesulfonates (triflates) with chromium(II) chloride under nickel catalysis" J Am Chem Soc. 108(19):6048-50 (1986).

(56) References Cited

OTHER PUBLICATIONS

AkzoNobel Polymer Chemicals, "Diisobutylaluminum hydride (DIBAL-H) and other isobutyl aluminum Alkyls (DIBAL-BOT, TIBAL) as specialty organic synthesis reagents," The AkzoNobel Technical Bulletin, 1-14 (2006).

Tokunaga et al., "Asymmetric catalysis with water: efficient kinetic resolution of terminal epoxides by means of catalytic hydrolysis," Science. 277(5328):936-8 (1997).

Towle et al. "Halichondrin B macrocyclic ketone analog E7389: medicinal chemistry repair of lactone ester instability generated during structural simplification to clinical Candidate" Annual Meeting of the American Association for Cancer Research, Apr. 6-10, 2002, 5721.

Towle et al. "In vitro and in vivo anticancer activities of synthetic macrocyclic ketone analogues of Halichondrin B," Cancer Res. 61(3):1013-21 (2001).

Uemura et al., "Norhalichondrin A: an antitumor polyether macrolide from a marine sponge," J Am Chem Soc. 107(16):4796-8 (1985).

Vahdat et al., "Phase II study of eribulin mesylate, a Halichondrin B analog, in patients with metastatic breast cancer previously treated with an anthracycline and a taxane," J Clin Oncol. 27(18):2954-61 (2009).

Varseev et al, "Enantioselective total synthesis of (+)-neosymbioimine," Org Lett. 9(8):1461-4 (2007).

Wan et al., "Asymmetric Ni(II)/Cr(II)-mediated coupling reaction: Stoichiometric process," Org Lett. 4(25):4431-4 (2002) Supporting Information, 8 pages.

Wang et al. "Structure-activity relationships of halichondrin B analogues: modifications at C.30-C.38" Bioorg Med Chem Lett. 10(10):1029-32 (2000).

Wang et al., "Facile preparation of peracetates and per-3-bromobenzoates of alpha-mono- and disaccharides," Molecules. 10(10):1325-34 (2005).

Xie et al., "Synthesis of the C20-C26 building block of Halichondrins via a regiospecific and stereoselective SN2' reaction," Org Lett. 4(25): 4427-9 (2002).

Yang et al., "Second generation synthesis of C27-C35 building block of E7389, a synthetic Halichondrin analogue," Org Lett. 11(20): 4516-9 (2009).

Youssefyeh, "Acylations of ketals and enol ethers," J Am Chem Soc. 85(23):3901-2 (1963).

Yu et al., "New synthetic route to the C.14-C.21 fragment of Halichondrin B," Book of Abstracts. 219th ACS National Meeting, San Francisco, CA, Mar. 26-30, 2000.

Yu et al., Discovery of E7389 a fully synthetic macrocyclic ketone analog of Halichondrin B. *Anticancer Agents from Natural Product*. CRC Press, 241-265 (2005).

Zheng et al., "Macrocyclic ketone analogues of halichondrin B," Bioorg Med Chem Lett. 14(22): 5551-4 (2004).

Zheng, W. et al. "Synthetic macrocyclic ketone analogs of halichondrin B: structure-activity relationships" Proceedings of the American Association for Cancer Research, 41:301, Abstract #1915 (2000).

U.S. Appl. No. 13/924,892, Austad et al.

Choi et al., "Supporting information for asymmetric Ni(II)/Cr(II)-mediated couple reaction: catalytic process," Org Lett. 4(25) (2002) (8 pages).

Kurosu et al., "Supporting information for Fe/Cr- and Co/Cr-mediated catalytic asymmetric 2-haloallylations of aldehydes," J Am Chem Soc. 126(39) (2004) (31 pages).

Namba et al., "New catalytic cycle for couplings of aldehydes with organochromium regeants," Org Lett. 6(26):5031-3 (2004).

* cited by examiner

METHODS USEFUL IN THE SYNTHESIS OF HALICHONDRIN B ANALOGS

The invention relates to methods useful in the synthesis of analogs of halichondrin B, in particular ER-086526, referred to under its generic name eribulin throughout the following specification.

BACKGROUND OF THE INVENTION

Eribulin (marketed under the trade name HALAVEN® as eribulin mesylate), a nontaxane microtubule dynamics inhibitor, is a structurally simplified, synthetic analog of the marine natural product halichondrin B. Methods for the synthesis of eribulin and other halichondrin B analogs are described in U.S. Pat. Nos. 6,214,865, 6,365,759, 6,469,182, 7,982,060, and 8,148,554, the syntheses of which are incorporated herein by reference. New methods for the synthesis of halichondrin B analogs, in particular eribulin and eribulin mesylate, are desirable.

SUMMARY OF THE INVENTION

In general, the present invention features improved methods useful for the synthesis of analogs of halichondrin B, such as eribulin and pharmaceutically acceptable salts thereof (e.g., eribulin mesylate).

In one aspect, the invention features a method of preparing an intermediate in the synthesis of eribulin including reacting a compound having formula (I):

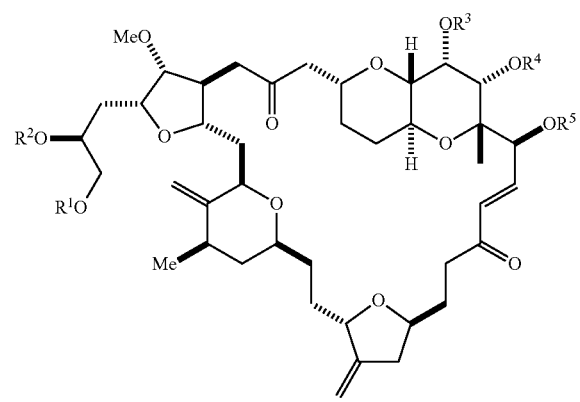

(I)

wherein each of $R^1$, $R^2$, $R^3$, $R^4$, and $R^5$ is independently a silyl group (e.g., trimethylsilyl (TMS), triethylsilyl (TES), t-butyldimethylsilyl (TBS), t-butyldiphenylsilyl (TBDPS), triisopropylsilyl (TIPS), or triphenylsilyl (TPS)), with a fluoride source (e.g., tetrabutylammonium fluoride) in a solvent including an amide, e.g., a N,N C1-C6 dialkyl C1-C6 alkyl amide or N C1-C6 alkyl C2-C6 lactam, such as N,N-dimethylacetamide (e.g., as a mixture of tetrahydrofuran and N,N-dimethylacetamide), N,N-dimethylformamide, N-methyl 2-pyrrolidone, N,N-diethylacetamide, or N,N-dimethylpropionamide, to produce the intermediate ER-811475:

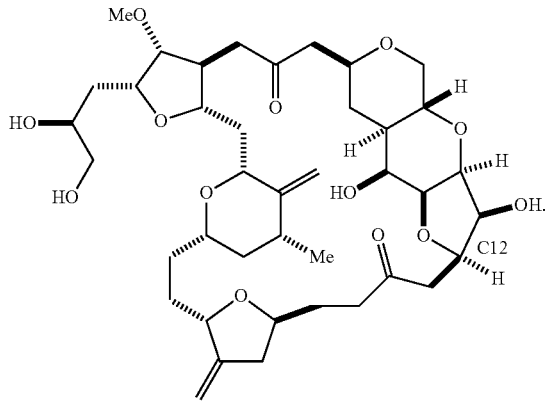

ER-811475

ER-811475 may be produced in a mixture with its C12 stereoisomer, ER-811474:

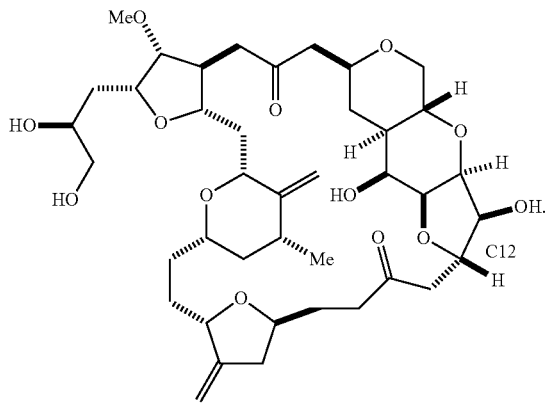

ER-811474

The method may further include adding a mixture of acetonitrile and water to increase the yield of ER-811475.

In some embodiments, each of $R^1$, $R^2$, $R^3$, $R^4$, and $R^5$ is t-butyldimethylsilyl (TBS).

The invention further features a method of preparing an intermediate in the synthesis of eribulin including reacting (e.g., in ethanol) ER-811475 with a conjugate acid of imidazole (e.g., imidazole hydrochloride) to produce the intermediate ER-076349:

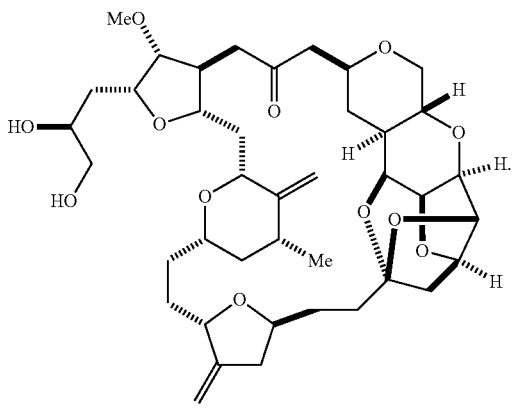

ER-076349

ER-811475 can be produced by any of the methods provided herein.

In another aspect, the invention features a method of preparing an intermediate in the synthesis of eribulin. This method includes reacting (e.g., in acetonitrile) ER-076349 with a sulfonylating reagent, e.g., tosyl chloride, in the presence of a metal catalyst (e.g., dibutyltin oxide) to produce the intermediate:

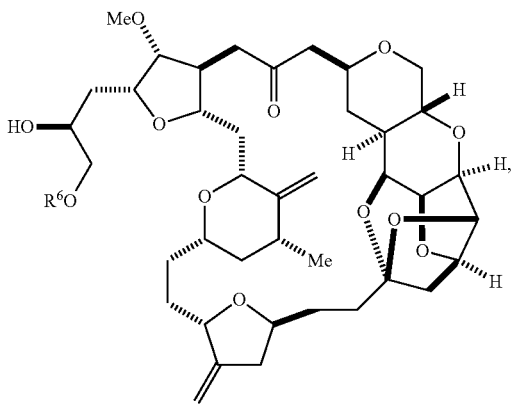

wherein $R_6$ is sulfonyl, e.g., ER-082892. The reacting may occur above 0° C. ER-076349 can be produced by any of the methods provided herein. The methods may also include addition of a base, e.g., a C1-6 trialkylamine, such as triethylamine or N,N-diisopropylethylamine.

The invention also features a method of producing eribulin. This method includes producing intermediate ER-811475 by any one of the foregoing methods, ketalizing ER-811475 to produce the intermediate ER-076349, and aminating ER-076349 to produce eribulin (ER-086526):

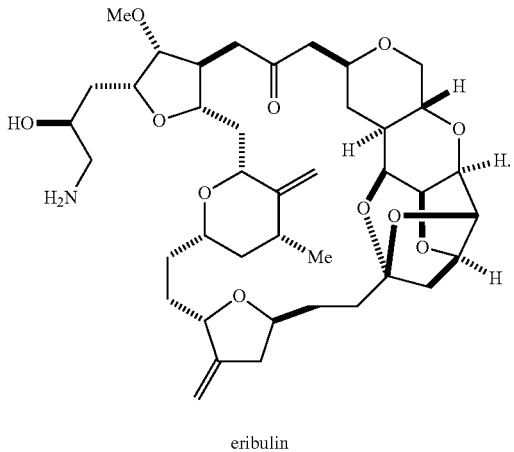

eribulin

The step of ketalizing ER-811475 may include converting ER-811475 to ER-076349 according to any of the methods provided herein. The step of aminating ER-076349 to produce eribulin may include converting ER-076349 to ER-082892 according to any of the methods provided herein. The invention further features an alternative method of producing eribulin. This method includes producing intermediate ER-076349 by any one of the foregoing methods and aminating ER-076349 to produce eribulin. The step of aminating ER-076349 to produce eribulin may include converting ER-076349 to ER-082892 according to any of the methods provided herein.

In a further aspect, the invention features yet another method of producing eribulin. This method includes producing intermediate ER-082892 by any of the methods provided herein and aminating ER-082892 to produce eribulin.

Any method of producing eribulin may further include salifying eribulin to produce a pharmaceutically acceptable salt of eribulin (e.g., eribulin mesylate).

The invention further features a method of manufacturing a pharmaceutical product including eribulin or a pharmaceutically acceptable salt thereof (e.g., eribulin mesylate). This method includes producing or directing the production of eribulin or a pharmaceutically acceptable salt thereof by any one of the foregoing methods and processing or directing the processing of eribulin or a pharmaceutically acceptable salt thereof into a pharmaceutical product including eribulin or a pharmaceutically acceptable salt thereof, thereby manufacturing a pharmaceutical product including eribulin or a pharmaceutically acceptable salt thereof.

The processing step can include one or more of formulating eribulin or a pharmaceutically acceptable salt thereof (e.g., eribulin mesylate); processing eribulin or a pharmaceutically acceptable salt thereof into a drug product; combining eribulin or a pharmaceutically acceptable salt thereof with a second component (e.g., an excipient or pharmaceutically acceptable carrier); lyophilizing eribulin or a pharmaceutically acceptable salt thereof; combining a first and second batch of eribulin or a pharmaceutically acceptable salt thereof to provide a third larger batch; disposing eribulin or a pharmaceutically acceptable salt thereof into a container (e.g., a gas or liquid tight container); packaging eribulin or a pharmaceutically acceptable salt thereof; associating a container including eribulin or a pharmaceutically acceptable salt thereof with a label; and shipping or moving eribulin or a pharmaceutically acceptable salt thereof to a different location.

For any of the following chemical definitions, a number following an atomic symbol indicates the total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted C2 alkyl group has the formula —$CH_2CH_3$. A reference to the number of oxygen, nitrogen, or sulfur atoms in a heteroaryl group only includes those atoms that form a part of a heterocyclic ring.

By "alkyl" is meant a straight or branched chain saturated cyclic (i.e., cycloalkyl) or acyclic hydrocarbon group of from 1 to 12 carbons, unless otherwise specified. Exemplary alkyl groups include C1-C8, C1-C6, C1-C4, C2-C7, C3-C12, and C3-C6 alkyl. Specific examples include methyl, ethyl, 1-propyl, 2-propyl (i.e., isopropyl), 2-methyl-1-propyl (i.e., isobutyl), 1-butyl, 2-butyl, 1,1-dimethylethyl (i.e., tert-butyl) and the like. Unless otherwise noted, alkyl groups, used in any context herein, are optionally substituted with halogen, alkoxy, aryloxy, arylalkyloxy, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, or azido.

By "alkylamino" is meant —NHR, wherein R is alkyl. By "[alkenyl]alkylamino" is meant —NRR', wherein R is alkyl, and R' is alkenyl. By "[aryl]alkylamino" is meant —NRR', wherein R is alkyl, and R' is aryl. By "[arylalkyl]alkylamino" is meant —NRR', wherein R is alkyl, and R' is arylalkyl. By "dialkylamino" is meant —NR$_2$, wherein each R is alkyl, selected independently.

By "alkylene" is meant a divalent alkyl group. Alkylene groups, used in any context herein, are optionally substituted in the same manner as alkyl groups. For example, an unsubstituted C1 alkylene group is —CH$_2$—.

By "alkylenedithio" is meant —S-alkylene-S—.

By "alkylthio" is meant —SR, wherein R is alkyl.

By "alkenyl" is meant a straight or branched chain cyclic or acyclic hydrocarbon group of, unless otherwise specified, from 2 to 12 carbons and containing one or more carbon-carbon double bonds. Exemplary alkenyl groups include C2-C8, C2-C7, C2-C6, C2-C4, C3-C12, and C3-C6 alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl groups, used in any context herein, are optionally substituted in the same manner as alkyl groups. Alkenyl groups, used in any context herein, may also be substituted with an aryl group.

By "alkoxy" is meant —OR, wherein R is alkyl.

By "aryl" is meant a monocyclic or multicyclic ring system having one or more aromatic rings, wherein the ring system is carbocyclic or heterocyclic. Heterocyclic aryl groups are also referred to as heteroaryl groups. A heteroaryl group includes 1 to 4 atoms selected independently from O, N, and S. Exemplary carbocyclic aryl groups include C6-C20, C6-C15, C6-C10, C8-C20, and C8-C15 aryl. A preferred aryl group is a C6-10 aryl group. Specific examples of carbocyclic aryl groups include phenyl, indanyl, indenyl, naphthyl, phenanthryl, anthracyl, and fluorenyl. Exemplary heteroaryl groups include monocylic rings having from 1 to 4 heteroatoms selected independently from O, N, and S and from 1 to 6 carbons (e.g., C1-C6, C1-C4, and C2-C6). Monocyclic heteroaryl groups preferably include from 5 to 9 ring members. Other heteroaryl groups preferably include from 4 to 19 carbon atoms (e.g., C4-C10). Specific examples of heteroaryl groups include pyridinyl, quinolinyl, dihydroquinolinyl, isoquinolinyl, quinazolinyl, dihydroquinazolyl, and tetrahydroquinazolyl. Unless otherwise specified, aryl groups, used in any context herein, are optionally substituted with alkyl, alkenyl, aryl, arylalkyl, halogen, alkoxy, aryloxy, arylalkyloxy, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, or azido.

By "arylalkyl" is meant —R'R", wherein R' is alkylene, and R" is aryl.

By "arylalkyloxy" is meant —OR, wherein R is arylalkyl.

By "aryloxy" is meant —OR, wherein R is aryl.

By "carboxyl" is meant —C(O)OH, in free acid, ionized, or salt form.

By "fluoride source" is meant a compound that can be a source of soluble fluoride ion (i.e., F$^-$) (e.g., to remove silyl ether hydroxyl protecting groups), exemplary fluoride sources include, ammonium fluoride, benzyltriethylammonium fluoride, cesium fluoride (i.e., CsF), 1-chloromethyl-4-fluoro-1,4-diazoniabicyclo[2.2.2]octane bis(tetrafluoroborate) (i.e., Selectfluor®), hydrofluoric acid (i.e., HF), poly[4-vinylpyridinium poly(hydrogen fluoride)], potassium fluoride (i.e., KF), pyridine hydrogen fluoride (i.e., HF-pyridine), sodium fluoride (i.e., NaF), tetrabutylammonium fluoride (i.e., TBAF), tetraethylammonium fluoride, tetramethylammonium fluoride, and tris(dimethylamino)sulfonium difluorotrimethylsilicate (i.e., TASF).

By "halogen" is meant fluoro, chloro, bromo, or iodo.

By "lactam" is meant a cyclic amide, wherein the ring consists of carbon atoms and one nitrogen atom.

By "leaving group" is meant a group that is displaced during a chemical reaction. Suitable leaving groups are well known in the art, e.g., see, *Advanced Organic Chemistry*, March, 4th Ed., pp. 351-357, John Wiley and Sons, N.Y. (1992). Such leaving groups include halogen, C1-C12 alkoxy (e.g., C1-C8, C1-C6, C1-C4, C2-C7, and C3-C6 alkoxy), C1-C12 alkylsulfonate (e.g., C1-C8, C1-C6, C1-C4, C2-C7, C3-C12, and C3-C6 alkylsulfonate), C2-C12 alkenylsulfonate (e.g., C2-C8, C2-C6, C2-C4, C3-C12, and C3-C6 alkenylsulfonate), carbocyclic C6-C20 arylsulfonate (e.g., C6-C15, C6-C10, C8-C20, and C8-C15 arylsulfonate), C4-C19 heteroarylsulfonate (e.g., C4-C10 heteroarylsulfonate), monocyclic C1-C6 heteroarylsulfonate (e.g., C1-C4 and C2-C6 heteroarylsulfonate), (C6-C15)aryl(C1-C6)alkylsulfonate, (C4-C19)heteroaryl(C1-C6)alkylsulfonate, (C1-C6)heteroaryl(C1-C6)alkylsulfonate, and diazonium. Alkylsulfonates, alkenylsulfonates, arylsulfonates, heteroarylsulfonates, arylalkylsulfonates, and heteroarylalkylsulfonates can be optionally substituted with halogen (e.g., chloro, iodo, bromo, or fluoro), alkoxy (e.g., C1-C6 alkoxy), aryloxy (e.g., C6-C15 aryloxy, C4-C19 heteroaryloxy, and C1-C6 heteroaryloxy), oxo, alkylthio (e.g., C1-C6 alkylthio), alkylenedithio (e.g., C1-C6 alkylenedithio), alkylamino (e.g., C1-C6 alkylamino), [alkenyl]alkylamino (e.g., [(C2-C6)alkenyl](C1-C6)alkylamino), [aryl]alkylamino (e.g., [(C6-C10)aryl](C1-C6)alkylamino, [(C1-C6)heteroaryl](C1-C6)alkylamino, and [(C4-C19)heteroaryl](C1-C6)alkylamino), [arylalkyl]alkylamino (e.g., [(C6-C10)aryl(C1-C6)alkyl](C1-C6)alkylamino, [(C1-C6)heteroaryl(C1-C6)alkyl](C1-C6)alkylamino, [(C4-C19)heteroaryl(C1-C6)alkyl](C1-C6)alkylamino), dialkylamino (e.g., di(C1-C6 alkyl)amino), silyl (e.g., tri(C1-C6 alkyl)silyl, tri(C6-C10 aryl or C1-C6 heteroaryl)silyl, di(C6-C10 aryl or C1-C6 heteroaryl)(C1-C6 alkyl)silyl, and (C6-C10 aryl or C1-C6 heteroaryl)di(C1-C6 alkyl)silyl), cyano, nitro, or azido. Alkenylsulfonates can be optionally substituted with carbocyclic aryl (e.g., C6-C15 aryl), monocyclic C1-C6 heteroaryl, or C4-C19 heteroaryl (e.g., C4-C10 heteroaryl). Arylsulfonates can be optionally substituted with alkyl (e.g., C1-C6 alkyl) or alkenyl (e.g., C2-C6 alkenyl). As defined herein, any heteroaryl group present in a leaving group has from 1 to 4 heteroatoms selected independently from O, N, and S. Specific examples of suitable leaving groups include chloro, iodo, bromo, fluoro, methanesulfonate (mesylate), 4-toluenesulfonate (tosylate), trifluoromethanesulfonate (triflate, OTf), nitro-phenylsulfonate (nosylate), and bromo-phenylsulfonate (brosylate). Leaving groups may also be further substituted as is known in the art.

By "oxo" or (O) is meant =O.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in Berge et al., *J. Pharmaceutical Sciences* 66:1-19, 1977 and *Pharmaceutical Salts: Properties, Selection, and Use*, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide (i.e., HBr), hydrochloride (i.e., HCl), hydroiodide (i.e., HI), 2-hydroxy-ethanesulfonate, lactobionate, lactate, laurate, lauryl sulfate, malate, maleate, malonate, methanesulfonate (i.e., mesylate), 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate (i.e., tosylate), undecanoate, valerate salts and the like.

By "silyl" is meant —SiR$_3$, wherein each R is independently alkyl, alkenyl, aryl, or arylalkyl. Examples of silyl groups include tri(C1-C6 alkyl)silyl, tri(C6-C10 aryl or C1-C6 heteroaryl)silyl, di(C6-C10 aryl or C1-C6 heteroaryl)(C1-C6 alkyl)silyl, and (C6-C10 aryl or C1-C6 heteroaryl)di(C1-C6 alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from O, N, and S. Silyl groups are known in the art, e.g., as described in *Greene's Protective Groups in Organic Synthesis*, Wiley-Interscience, 4$^{th}$ Edition, 2006. Specific examples of silyl groups include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. Silyl groups may be substituted as is known in the art; for example, aryl and arylalkyl groups, such as phenyl, benzyl, naphthyl, or pyridinyl, can be substituted with C1-C6 alkyl, C1-C6 alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups.

By "sulfonyl" is meant —S(O)$_2$R, wherein R is alkyl, alkenyl, aryl, arylalkyl, or silyl. In exemplary sulfonyl groups, R is C1-C12 alkyl (e.g., C1-C8, C1-C6, C1-C4, C2-C7, C3-C12, and C3-C6 alkyl), C2-C12 alkenyl (e.g., C2-C8, C2-C6, C2-C4, C3-C12, and C3-C6 alkenyl), carbocyclic C6-C20 aryl (e.g., C6-C15, C6-C10, C8-C20, and C8-C15 aryl), monocyclic C1-C6 heteroaryl (e.g., C1-C4 and C2-C6 heteroaryl), C4-C19 heteroaryl (e.g., C4-C10 heteroaryl), (C6-C15)aryl(C1-C6)alkyl, (C4-C19)heteroaryl(C1-C6)alkyl, or (C1-C6)heteroaryl(C1-C6)alkyl. As defined herein, any heteroaryl group present in a sulfonyl group has from 1 to 4 heteroatoms selected independently from O, N, and S. Exemplary sulfonyl groups include tosyl, triflyl, and mesyl.

Other features and advantages of the invention will be apparent from the following description and the claims.

DETAILED DESCRIPTION OF THE INVENTION

The present invention provides methods for the synthesis of halichondrin B analogs. In particular, the methods are useful for the synthesis of eribulin and pharmaceutically acceptable salts thereof:

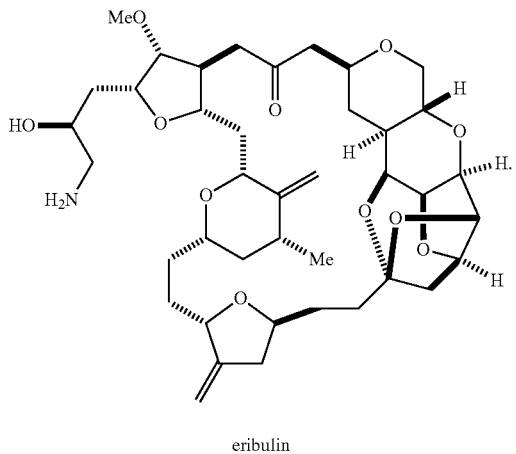

eribulin

Synthesis of Compounds of Formula (I)

Compounds of formula (I):

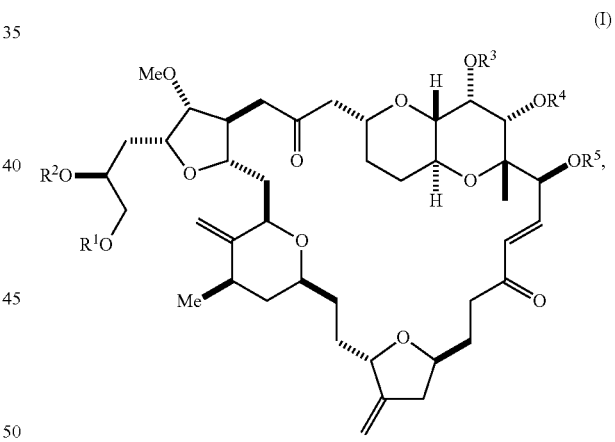

can be synthesized using methods known in the art (e.g., as described in U.S. Pat. Nos. 6,214,865, 6,365,759, 6,469,182, 7,982,060, and 8,148,554, International Publication Nos. WO 99/65894, WO 2005/118565, and WO 2011/094339, Chase et al. Syn. Lett. 2013; 24(3):323-326, Austad et al. Syn. Lett. 2013; 24(3):327-332, and Austad et al. Syn. Lett. 2013; 24(3): 333-337, the syntheses of which are incorporated herein by reference). In one example, the C14-C35 portion (e.g., ER-804028) of the molecule is coupled to the C1-C13 portion (e.g., ER-803896) to produce the C1-C35 acyclic intermediate (e.g., ER-804029), and additional reactions are carried out to produce a compound of formula (I) (e.g., ER-118046) as shown in Scheme 1:

Scheme 1

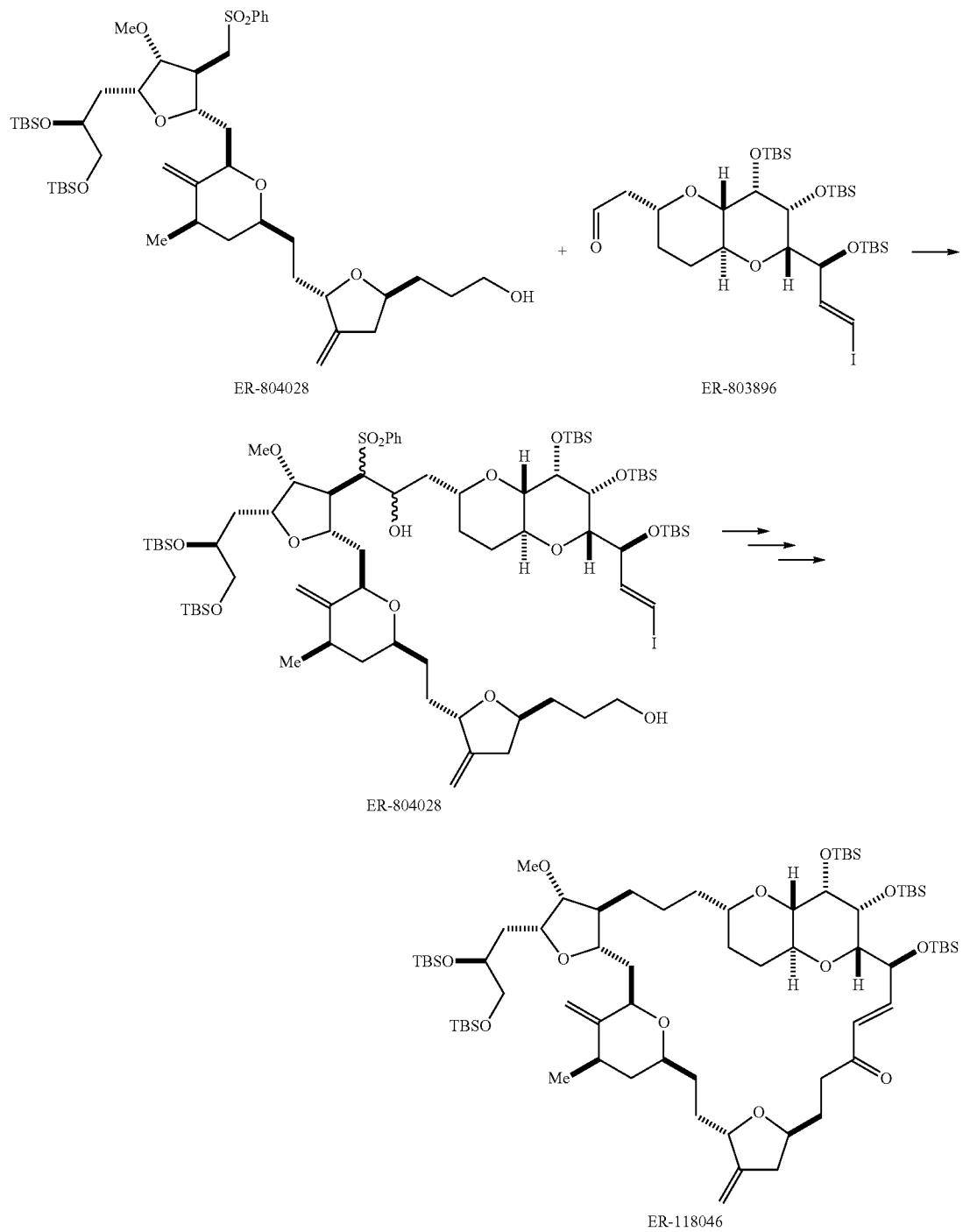

Other compounds of Formula I can be produced by using different protecting groups in the C1-C13 and/or C14-C35 fragments.

In one specific example, deprotonation, e.g., by lithiation, of the C14-C35 sulfone fragment (i.e., ER-804028) followed by coupling to the C1-C13 aldehyde fragment (i.e., ER-803896) furnishes a mixture of diastereomeric alcohols (i.e., ER-804029). Additional protecting group manipulation and oxidation followed by removal of the sulfonyl group and an intramolecular Nozaki-Hiyama-Kishi (NHK) reaction affords an intermediate, which, when oxidized furnishes a compound of formula (I) (i.e., ER-118046).

Conversion of a Compound of Formula (I) to Eribulin

A scheme for converting a compound of formula (I) to eribulin is as follows (Scheme 2).

Scheme 2
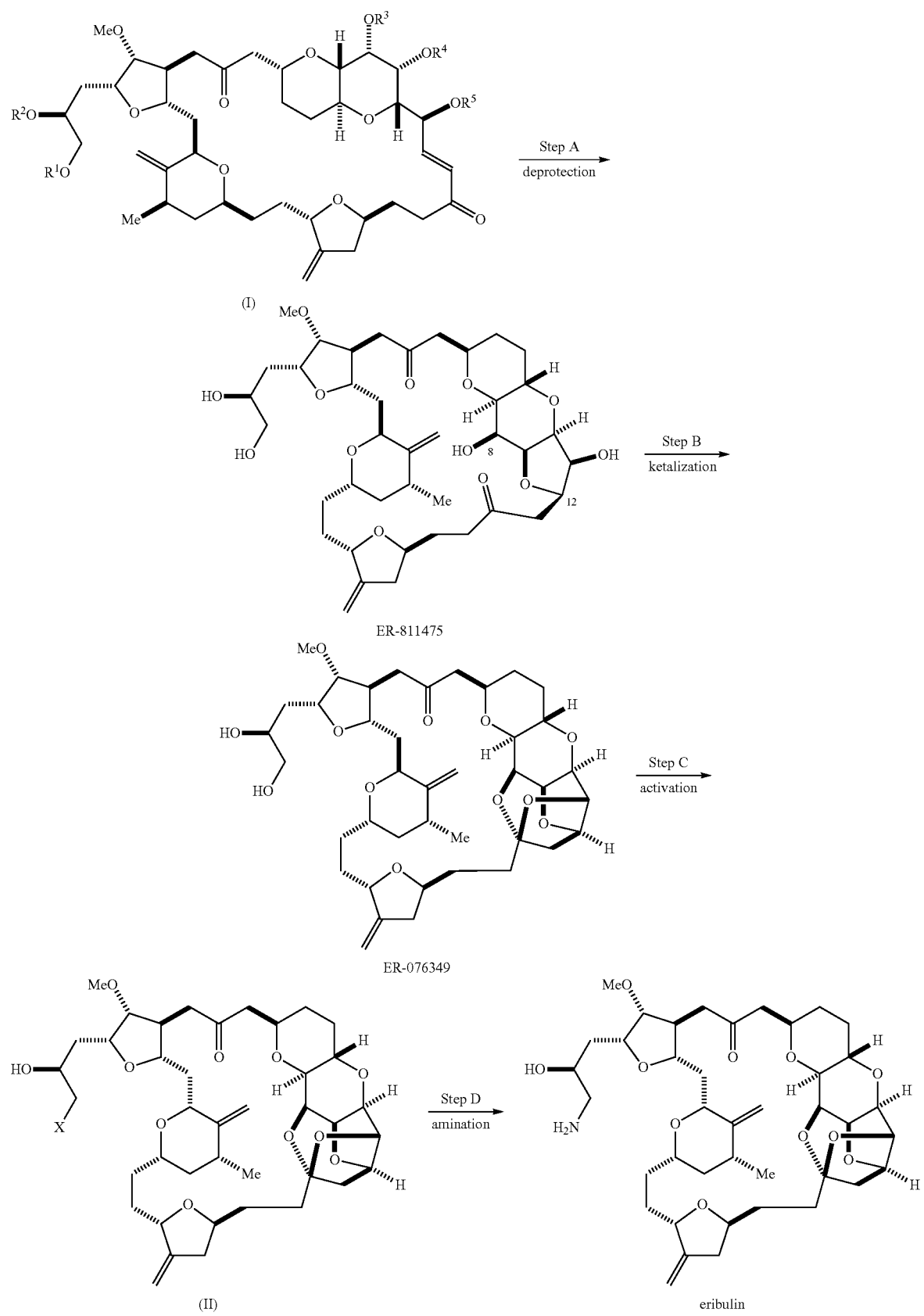

As outlined in Scheme 2, deprotection of the silyl ether hydroxyl protecting groups (i.e., $R^1$, $R^2$, $R^3$, $R^4$, and $R^5$) of a compound of formula (I) followed by equilibration furnishes ER-811475 (Step A). Ketalization of ER-811475 provides ER-076349 (Step B). Activation of the C35 primary alcohol (e.g., as the C35 tosylate) resulting in a compound of formula (II), wherein X is a leaving group (e.g., halogen, mesylate, or tosylate) (Step C), followed by introduction of the amine functionality, provides eribulin (Step D). One skilled in the art would also understand that variations on the above scheme are possible.

Step a: Conversion of a Compound of Formula (I) to ER-811475

Method A1: Deprotection with Fluoride Source in THF

One method for the conversion of a compound of formula (I) to ER-811475 is shown in Scheme 3:

Scheme 3

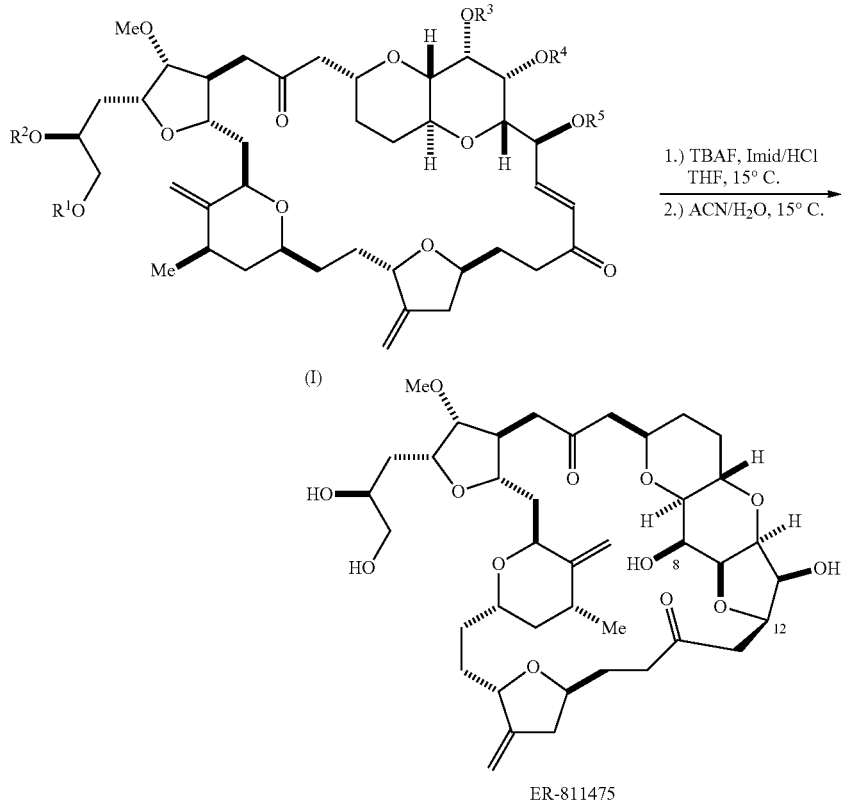

Treatment of a compound of formula (I) with a fluoride source (e.g., tetrabutylammonium fluoride) and equilibration with a conjugate acid of imidazole (e.g., imidazole hydrochloride), in tetrahydrofuran as solvent, results in ER-811475 in a 4:1 mixture with its C12 stereoisomer ER-811474.

Method A2: Deprotection with Fluoride Source in an Amide, e.g., DMAC

An alternative method for the conversion of a compound of formula (I) to ER-811475 is shown in Scheme 4:

Scheme 4

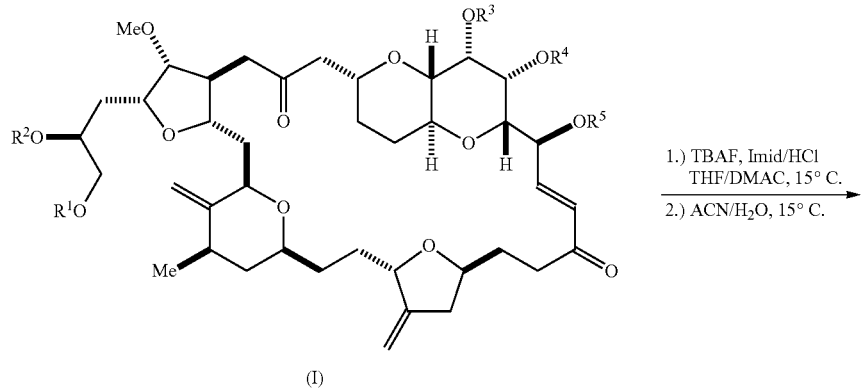

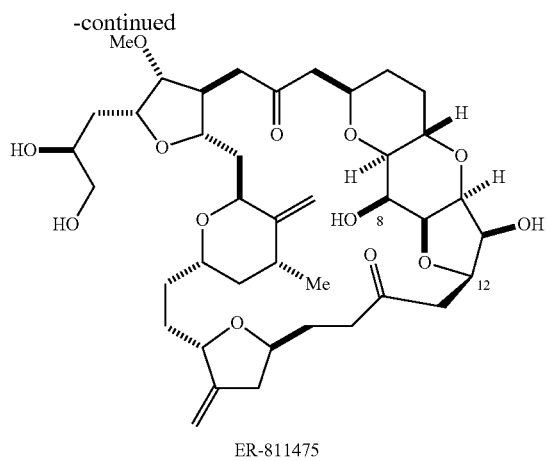
ER-811475

Treatment of a compound of formula (I) with a fluoride source (e.g., tetrabutylammonium fluoride) and equilibration with a conjugate acid of imidazole (e.g., imidazole hydrochloride), in an amide, e.g., N,N-dimethylacetamide (DMAC), as solvent (e.g., a mixture of tetrahyrofuran (THF) and DMAC), results in ER-811475. The addition of DMAC as co-solvent in the reaction results in improved selectivity at C12 (e.g., 18:1 vs. 4:1) and shortened reaction time (e.g., 1-2 days from 7-10 days). The addition of the mixture of acetonitrile and water increases the yield of ER-811475. Other amides include an N,N C1-C6 dialkyl C1-C6 alkyl amide or N C1-C6 alkyl C2-C6 lactam, such as N,N-dimethylformamide, N-methyl 2-pyrrolidone, N,N-diethylacetamide, or N,N-dimethylpropionamide may also be employed.

Step B: Ketalization of ER-811475 to ER-076349

Method B1: Ketalization with Conjugate Acid of Pyridine

A method for the ketalization of ER-811475 is shown in Scheme 5:

Scheme 5

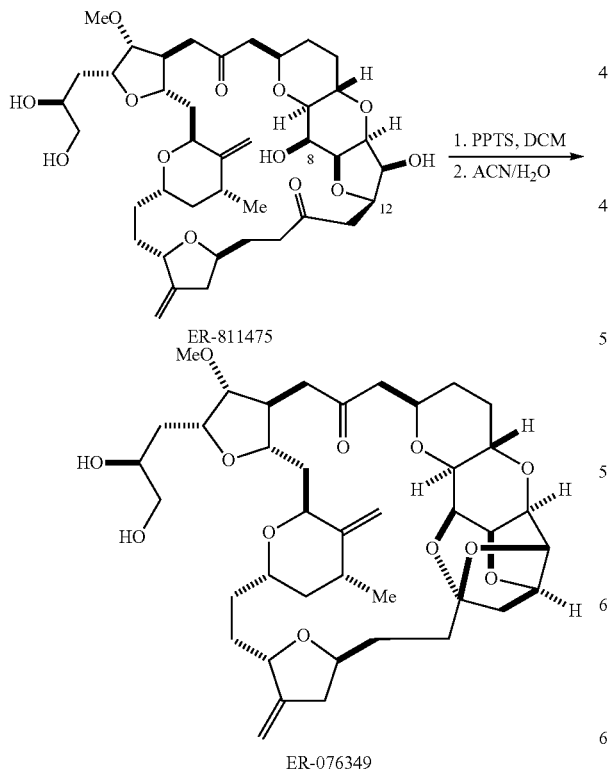

Ketalization of ER-811475 (e.g., in dichloromethane) with a conjugate acid of pyridine (e.g., pyridinium p-toluenesulfonate (PPTS)), followed by crystallization from acetonitrile and water, provides ER-076349.

Method B2: Ketalization with Conjugate Acid of Imidazole

An alternative method for the ketalization of ER-811475 to ER-076349 is shown in Scheme 6:

Scheme 6

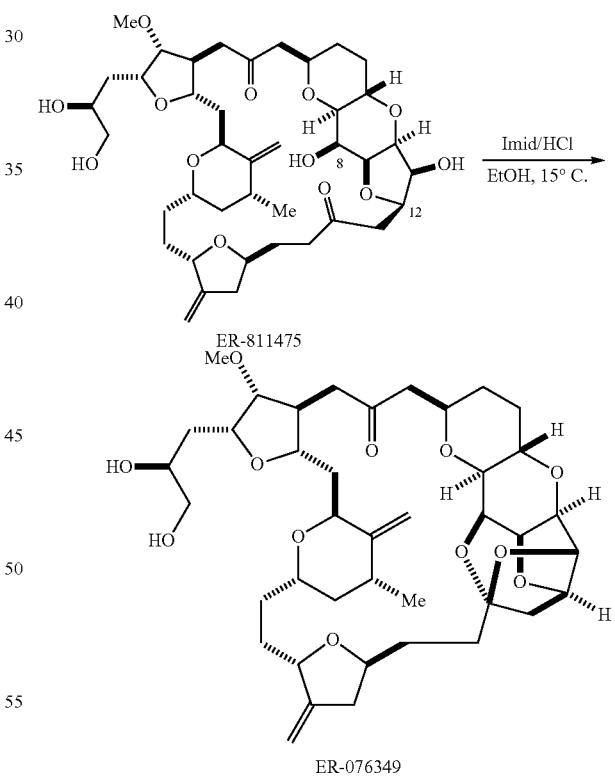

Conversion of ER-811475 to ER-076349 can be achieved through ketalization of ER-811475 (e.g., in ethanol) with a conjugate acid of imidazole (e.g., imidazole hydrochloride), followed by column chromatography. Replacing PPTS with imidazole hydrochloride results in a decrease of isomerization at C12 during post-processing (e.g., concentration of the reaction mixture). Changing of the solvent from dichloromethane to ethanol results in a more environmentally favorable process.

Step C: Activation of ER-076349 to a Compound of Formula (II)

Method C1: Activation with Tosyl Chloride and Pyridine

A method for the activation of ER-076342 is shown in Scheme 7:

Scheme 7

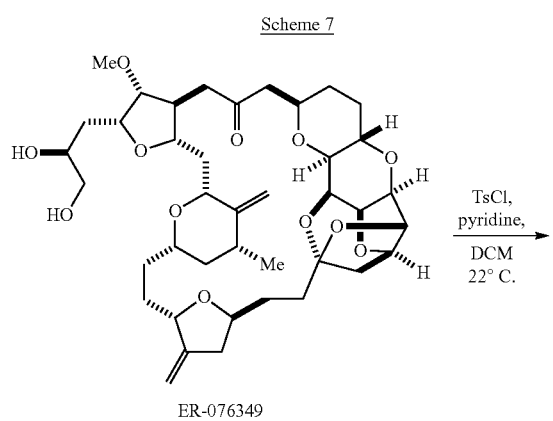

ER-076349

TsCl, pyridine, DCM 22° C.

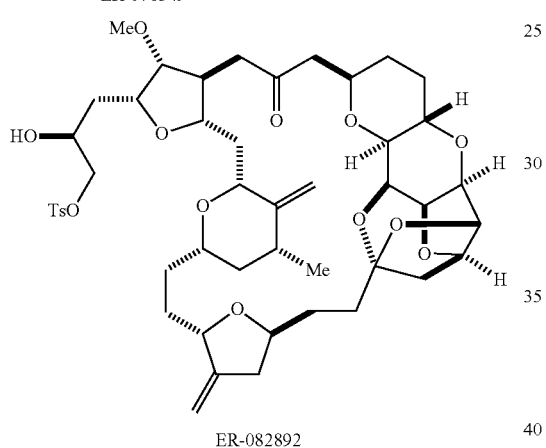

ER-082892

Reacting ER-076349 (e.g., in dichloromethane) with tosyl chloride and a base (e.g., pyridine) at 22° C. provides a compound of formula (II) (i.e., ER-082892).

Method C2: Activation with Ts₂O, Collidine, and Pyridine

An alternative method for the activation of ER-076349 is shown in Scheme 8:

Scheme 8

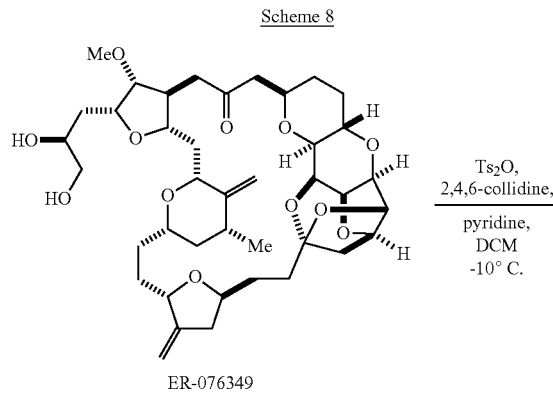

ER-076349

Ts₂O, 2,4,6-collidine, pyridine, DCM −10° C.

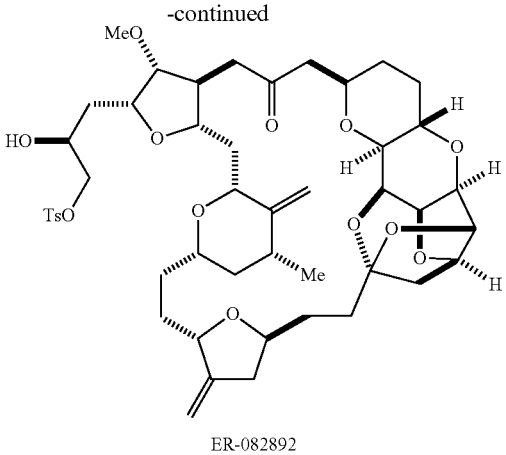

ER-082892

Treatment of ER-076349 (e.g., in dichloromethane) with 4-toluenesulfonic anhydride (Ts₂O), and base (e.g., a combination of 2,4,6-collidine and pyridine) at −10° C. provides a compound of formula (II) (i.e., ER-082892).

Method C3: Activation with Mesyl Chloride

Another method for the activation of ER-076349 is shown in Scheme 9:

Scheme 9

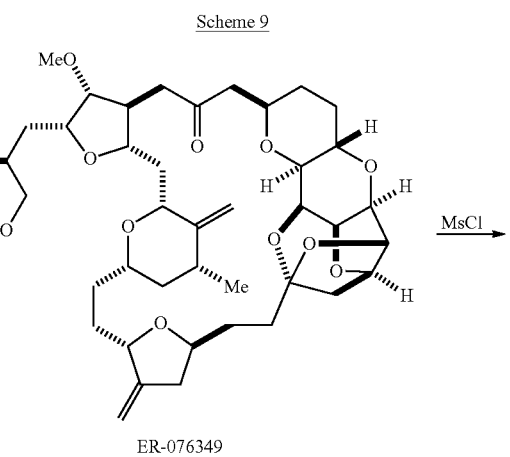

ER-076349

MsCl

B-2294

Reacting ER-076349 (e.g., in dichloromethane) with mesyl chloride and a base (e.g., 2,4,6-collidine) at 0° C. provides a compound of formula (II) (i.e., B-2294).

Method C4: Activation with Tosyl Chloride and Base

Another method for the activation of ER-076349 is shown in Scheme 10:

Scheme 10

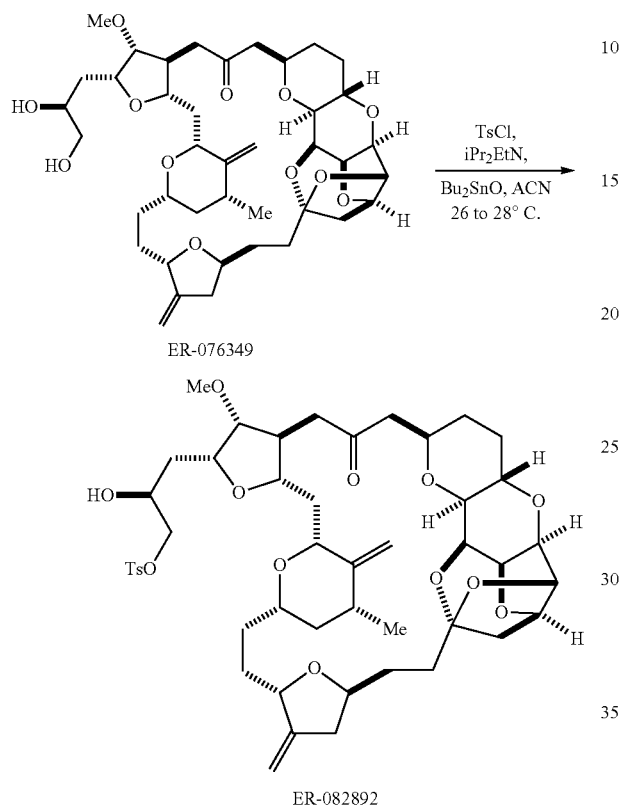

ER-076349

ER-082892

The activation of ER-076349 (e.g., in acetonitrile) can be achieved by treatment (e.g., at 26 to 28° C.) with tosyl chloride and a base (e.g., a C1-C6 trialkylamine, such as triethylamine and N,N-diisopropylethylamine) in the presence of a catalyst (e.g., dibutyltin oxide). The use of dibutyltin oxide, for example, makes the process more robust (e.g., reduces reaction sensitivity to moisture) and improves process operational efficiency (e.g., by elimination of an azeotropic drying step). Replacing pyridine and/or collidine with N,N-diisopropylethylamine and the addition of dibutyltin oxide as a catalyst provide an improvement in selectivity for primary alcohol (e.g., the mono-tosylation:di-tosylation ratio improved from 96:4 to 99.8:0.2). The replacement of dichloromethane with acetonitrile as solvent results in a more environmentally favorable process, and the change in temperature from −10° C. to 26° C.-28° C. increases operational efficiency and yield.

Step D: Amination of a Compound of Formula (II) to Eribulin

Method D1: Staudinger Route

A method for the amination of a compound of formula (II) is shown in Scheme 11, wherein X is a leaving group (e.g., OTs):

Scheme 11

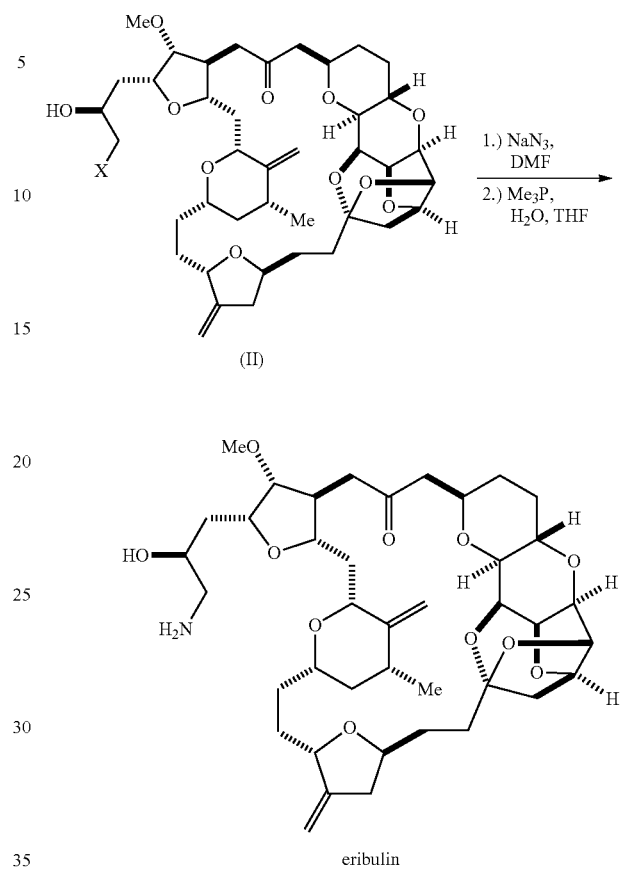

(II)

eribulin

The amination of a compound of formula (II) (e.g., ER-082892) to eribulin can be achieved through treatment with sodium azide, followed by reduction of the resulting azide with trimethylphosphine under Staudinger reaction conditions.

Method D2: Epoxide Opening Route

An alternative method for the amination of a compound of formula (II) to eribulin is shown in Scheme 12, wherein X is a leaving group (e.g., OTs):

Scheme 12

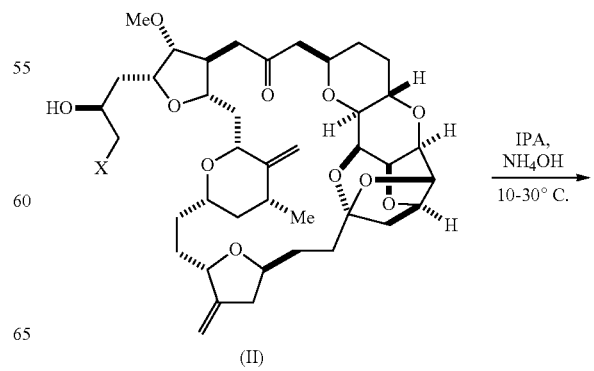

(II)

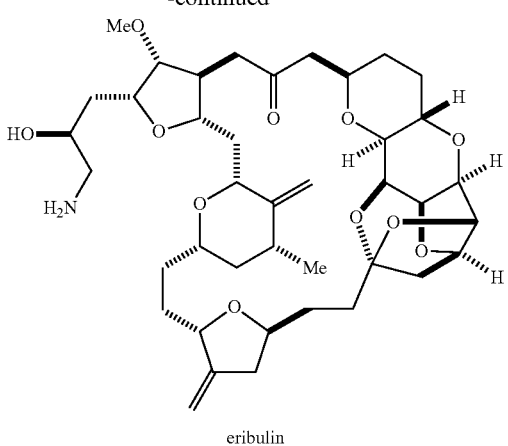

eribulin

In this method, the amination of a compound of formula (II) (e.g., ER-082892) can be accomplished through treatment with alcoholic ammonium hydroxide resulting in cyclization to an epoxide in situ that reacts further with ammonia to provide eribulin. Replacement of the Staudinger route with the epoxide opening route results in the elimination of the use of hazardous reagents and an increase in operational efficiency.

Salification of Eribulin

Pharmaceutically acceptable salts of eribulin (e.g., eribulin mesylate) can be formed by methods known in the art (e.g., in situ during the final isolation and purification of the compound or separately by reacting the free base group with a suitable acid). In one example, eribulin is treated with a solution of methanesulfonic acid (i.e., MsOH) and ammonium hydroxide in water and acetonitrile. The mixture is concentrated. The residue is dissolved in dichloromethane-pentane, and the solution is added to anhydrous pentane. The resulting precipitate is filtered and dried under high vacuum to provide eribulin mesylate, as shown in Scheme 13.

Scheme 13

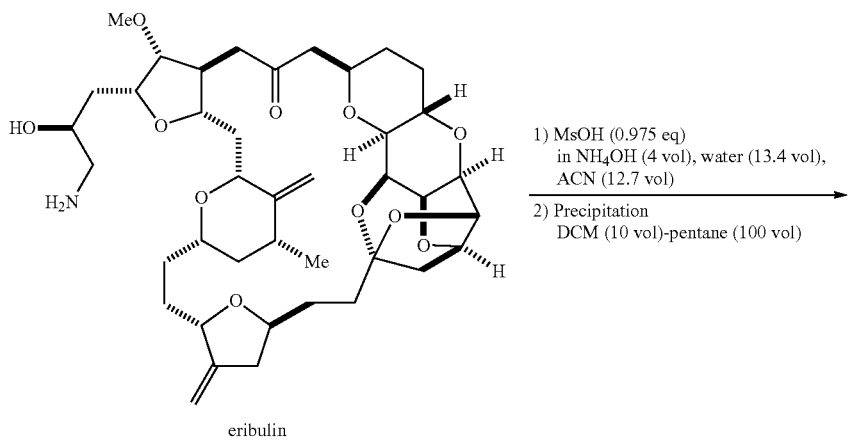

eribulin

1) MsOH (0.975 eq) in NH₄OH (4 vol), water (13.4 vol), ACN (12.7 vol)

2) Precipitation DCM (10 vol)-pentane (100 vol)

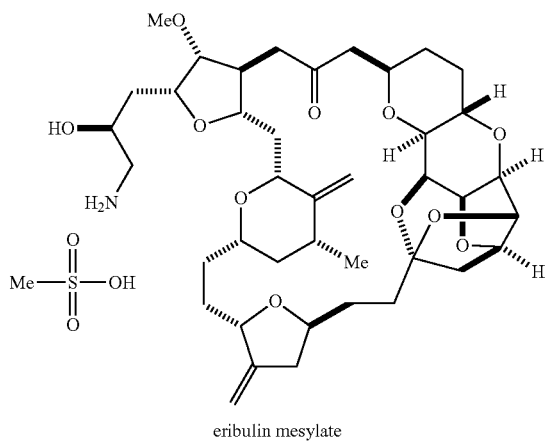

eribulin mesylate

Any combination of the methods described above for the synthesis of the various intermediates can be utilized to convert a compound of formula (I) to eribulin (e.g., Methods A1-B2-C1-D1, A1-B2-C2-D1, A1-B2-C1-D2, A2-B1-C1-D1, A2-B2-C1-D1, A2-B1-C2-D1, A2-B1-C1-D2, A2-B2-C2-D1, A2-B2-C1-D2, A2-B1-C2-D2, A2-B2-C2-D2, A2-B1-C3-D1, A1-B2-C3-D1, A2-B2-C3-D1, A2-B1-C3-D2, A1-B2-C3-D2, A2-B2-C3-D2, A1-B1-C4-D1, A2-B1-C4-D1, A1-B2-C4-D1, A1-B1-C4-D2, A2-B2-C4-D1, A2-B1-C4-D2, A1-B2-C4-D2, and A2-B2-C4-D2,).

EXPERIMENTAL PROCEDURES

Step A: Conversion of ER-118046 to ER-811475

Method A1

ER-811475: (1R,2S,3S,4S,5S,6RS,11S,14S,17S, 19R,21R,23S,25R,26R,27S,31R,34S)-25-[(2S)-2,3-Dihydroxypropyl]-2,5-dihydroxy-26-methoxy-19-methyl-13,20-bis(methylene)-24,35,36,37,38,39-hexaoxaheptacyclo[29.3.1.13,6.14,34.111,14.117, 21.023,27]nonatriacontane-8,29-dione The solution of ER-118046 (0.580 kg, 0.439 mol, 1 eq) in n-heptane was concentrated in vacuo at ≤50° C. The residue was dissolved in anhydrous tetrahydrofuran (THF) (19.7 L) and treated with tetrabutyl ammonium fluoride (TBAF) (1.0 M solution in THF, 2.85 L, 2.85 mol, 6.5 eq) buffered with imidazole hydrochloride (0.142 kg, 1.36 mol, 3.1 eq) at 10-25° C. Upon confirmation of the level of C34/C35-diol (≤3%), toluene (7.6 kg) and water (8.7 kg) were added for extraction. The aqueous layer was separated and extracted with toluene (5.0 kg) and THF (5.2 kg). The aqueous layer was drained, and the organic layer was combined with the first extract. The combined organic layers were concentrated in vacuo at ≤35° C. During the concentration, the free pentaol was converted to ER-811475 and ER-811474. When the residual level of free pentaol was ≥5%, acetonitrile (ACN) (3.3 kg) and water (0.42 kg) were added and azeotroped in vacuo<35° C. until the level came down to <5%. Upon completion, the residue was further azeotroped in vacuo with acetonitrile (4.6 kg)<35° C. The residue was diluted with dichloromethane (7.7 kg) and azeotroped in vacuo<35° C. to give a mixture of ER-811475 and ER-811474 (4:1).

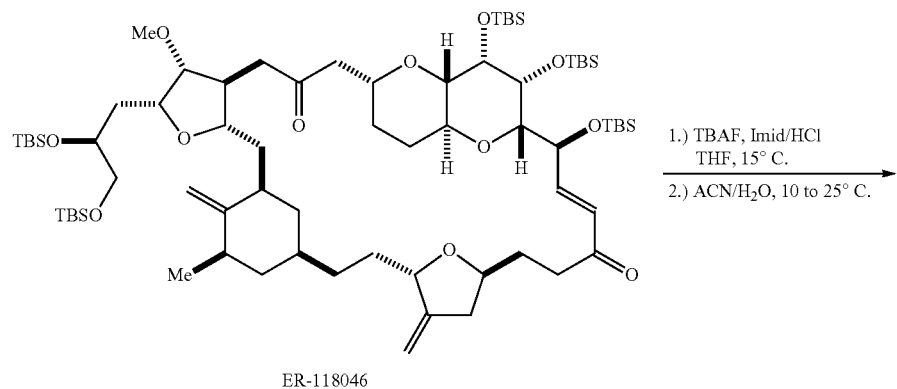

ER-118046

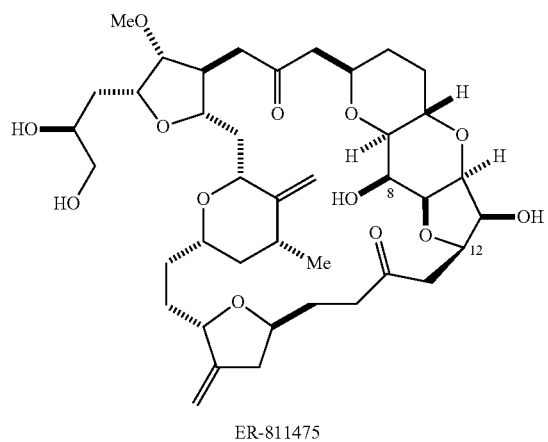

ER-811475

Method A2

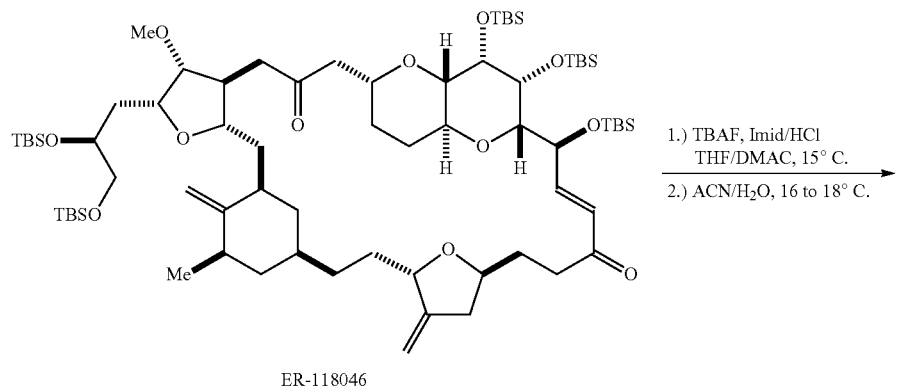

ER-118046

1.) TBAF, Imid/HCl
    THF/DMAC, 15° C.
2.) ACN/H₂O, 16 to 18° C.

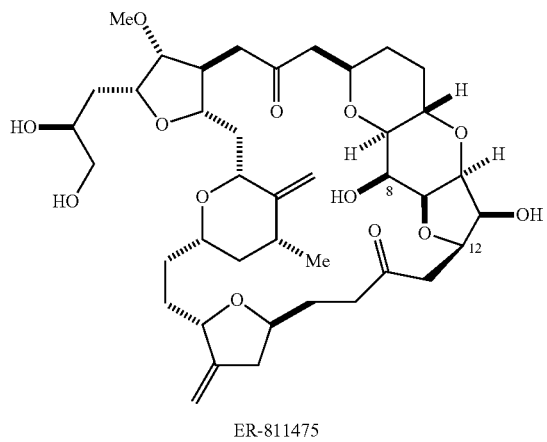

ER-811475

The solution of enone ER-118046 (135 g) in n-heptane was concentrated in vacuo at 41° C. or below. The residue was dissolved in anhydrous tetrahydrofuran (THF) (2.03 L) and N,N-dimethylacetamide (675 mL) and then treated with tetrabutylammonium fluoride (TBAF) (0.97 mol/L solution in THF, 685 mL) buffered with imidazole HCl (31.5 g) at 16° C. to 18° C. The mixture was stirred at 16° C. to 18° C. for 47 hours, and the reaction progress was monitored by HPLC. After the residual level of the reaction intermediate C34/C35-diol reached 3% or below, acetonitrile (608 mL) and water (203 mL) were added. The mixture was stirred at 16° C. to 18° C. for 45 hours until the residual level of free pentaol came down to below 5%. The reaction mixture including ER-811475/ER-811474 (a mixture of two diastereomers 18:1) could be used for the next stage without further purification.

Step B: Ketalization of ER-811475 to ER-076349

Method B1

ER-076349: (1S,3S,6S,9S,12S,14R,16R,18S,20R, 21R,22S,26R,29S,31R,32S,33R,35R,36S)-20-[(2S)-2,3-Dihydroxypropyl]-21-methoxy-14-methyl-8,15-bis(methylene)-2,19,30,34,37,39,40,41-octaoxanonacyclo[24.9.2.13,32.13,33.16,9.112, 16.018,22.029,36.031,35]hentetracontan-24-one

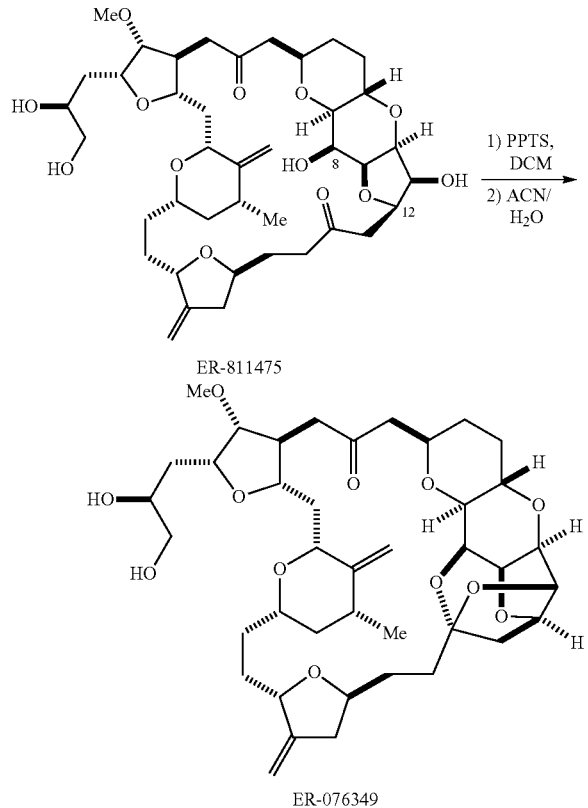

ER-811475 in a mixture with ER-811474 (0.329 kg, 0.439 mol, 1 eq) was dissolved in dichloromethane (DCM; 7.7 kg) and treated with a pyridinium p-toluenesulfonate (PPTS; 0.607 kg, 2.42 mol, 5.5 eq) solution in dichloromethane (1.7 kg) at 10-20° C. The resulting mixture was stirred at 10-20° C. The major diastereomer reacted to provide diol ER-076349, and the minor diastereomer ER-811474 remained unreacted. When the residual level of ER-811475 was >1%, additional PPTS (0.055 kg) in dichloromethane (0.15 kg) was added, and the reaction was continued at 10-20° C. Upon completion, the reaction mixture was directly loaded onto a silica gel column that was pre-equilibrated with methyl t-butyl ether (MTBE) (200 L). The reactor was further rinsed with dichloromethane (3.1 kg), and the rinse was loaded onto the column. The column was eluted sequentially with: (1) methyl t-butyl ether (125 L), (2) 96% v/v methyl t-butyl ether in acetonitrile (125 L), (3) 50% v/v methyl t-butyl ether in acetonitrile (250 L), and (4) acetonitrile (225 L). Desired fractions were combined, concentrated in vacuo<35° C., and azeotroped in vacuo with acetonitrile (4.6 kg)<35° C. The residue was dissolved in acetonitrile (0.32 kg) and water (0.54 kg) and subjected to crystallization with ER-076349 seed crystals (0.27 g, 0.36 mmol) and additional water (2.70 kg). The resulting crystals were filtered, and the weight of the filtrate was monitored until the recovery ratio to the crystallization solvent was reached ≥80%. The crystals were further washed with water (2.7 kg) and dissolved in dichloromethane (10.8 kg), and the solution was concentrated in vacuo at ≤25° C. The residue was diluted with acetonitrile (2.1 kg) and concentrated in vacuo at ≤40° C. to give ER-076349 (55-75% yield from ER-118046).

Method B2

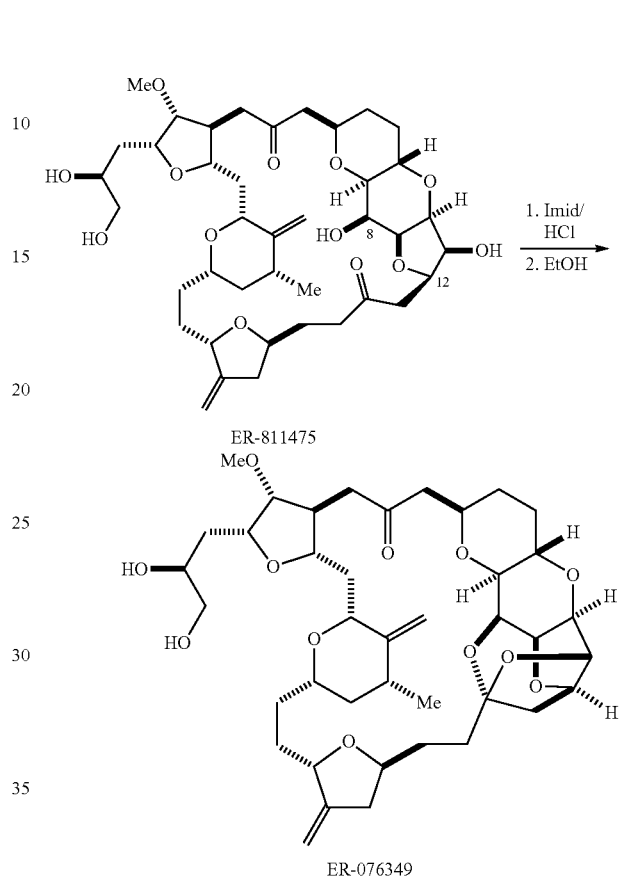

To ER-811475 (in a mixture with ER-811474), a solution of imidazole HCl (85.5 g) in water (68 mL) was added. The solution was concentrated in vacuo at 28° C. or below. The residue was dissolved in EtOH (2.69 kg). The resulting mixture was stirred at 21° C. to 24° C. for 43 hours. The major diastereomer (ER-811475) reacted to provide diol ER-076349, and the minor diastereomer (ER-811474) remains unreacted. The reaction was monitored for a disappearance of ER-811475 by HPLC. After the residual level of ER-811475 reached below 1%, the solution was concentrated in vacuo at 37° C. or below. Toluene (1.35 L) was added, and the solution was azeotroped in vacuo at 37° C. or below. Tetrahydrofuran (THF) (4.20 kg), toluene (1.76 kg), and water (2.03 L) were added and extracted. The aqueous layer was separated, and the organic layer was washed with water (1.01 L). The aqueous layers were combined and extracted with toluene (1.18 kg) and THF (1.20 kg). The aqueous layer was drained, and the organic layer was combined with the first extract. The combined organic layers were concentrated in vacuo at 37° C. or below. Toluene (675 mL) was added, and the solution was azeotroped in vacuo at 38° C. or below. The concentrate was diluted with dichloromethane (1.01 L) and then loaded onto a silica gel column (5.511 kg) pre-equilibrated with methyl t-butyl ether (more than 55.1 L). The column was eluted sequentially with methyl t-butyl ether (40.8 L), 95% v/v methyl t-butyl ether in acetonitrile (24.9 L), 40% v/v methyl t-butyl ether in acetonitrile (83.6 L), and acetonitrile (76.3 L) to remove the unreacted intermediates, the reaction impurities, and the carryover impurities from ER-804028. Desired fractions were combined and concentrated in vacuo at 32° C. or below to give ER-076349 (assay 62.02 g, yield over two steps 84.0%). The residue was azeotroped in vacuo with acetonitrile (0.533 kg) at 29° C. or below and could be used for the next stage without further purification.

Steps C and D: Conversion of ER-076349 to Eribulin

Methods C2+D2 eribulin: (1S,3S,6S,9S,12S,14R,16R,18S,20R,21R, 22S,26R,29S,31R,32S,33R,35R,36S)-20-[(2S)-3-Amino-2-hydroxypropyl]-21-methoxy-14-methyl-8, 15-bis(methylene)-2,19,30,34,37,39,40,41-octaoxanonacyclo[24.9.2.1³,³².1³³,¹⁶.9.1¹², 16.0¹⁸,²².0²⁹,³⁶.0³¹,³⁵]hentetracontan-24-one

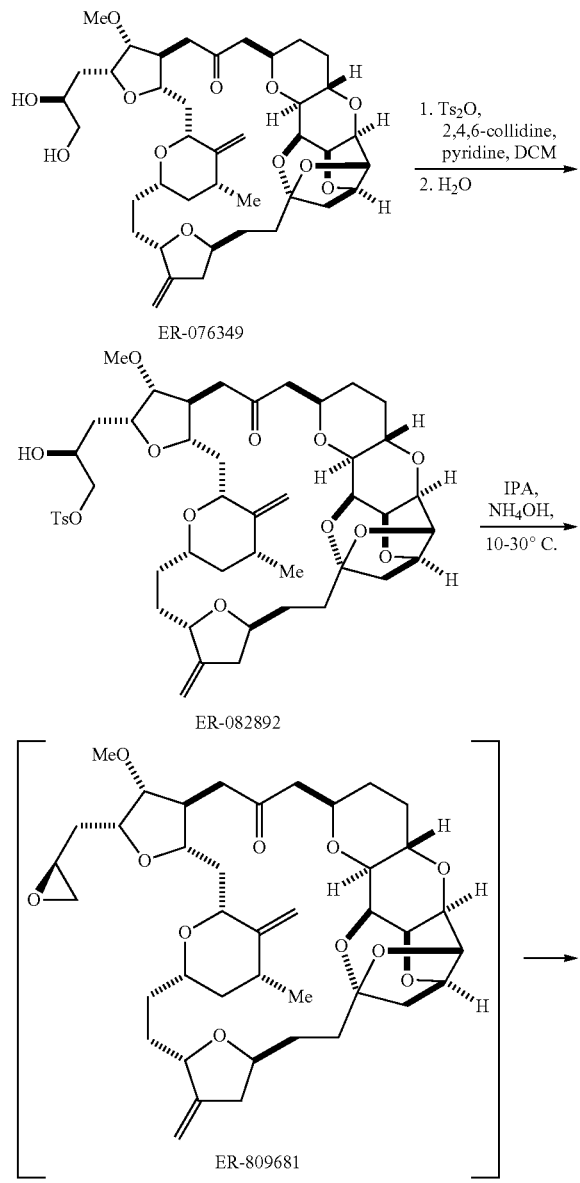

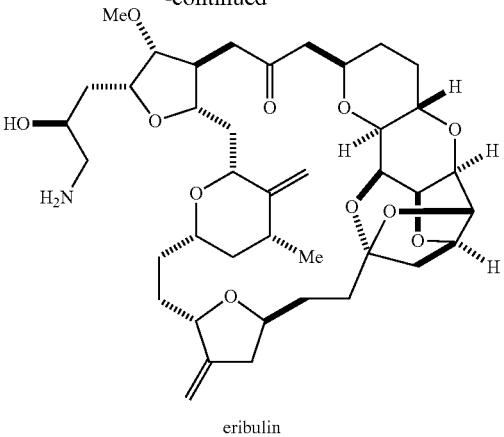

eribulin

ER-076349 (0.259 kg, 0.354 mol, 1 eq) was dissolved in toluene (4.7 kg) and azeotroped in vacuo at <25° C. The residue was diluted with toluene (4.5 kg) to give a toluene solution for monitoring of water content. Water content was measured by Karl-Fischer (KF) titration method. If the KF value was >125 ppm, the solution was azeotroped in vacuo at <25° C. and diluted with toluene (4.5 kg) until the water content came down to 125 ppm. If the KF value reached the target value, the solution was concentrated and dissolved in anhydrous dichloromethane (6.5 kg). 2,4,6-collidine (0.172 kg, 1.27 mol, 4 eq) and pyridine (0.0014 g, 0.018 mol, 0.05 eq) in anhydrous dichloromethane (84.1 g) were added, and the mixture was cooled. A solution of $Ts_2O$ (0.124 kg, 0.380 mol, 1.07 eq) in anhydrous dichloromethane (3.4 kg) was added to the reaction mixture at a rate to maintain the reaction temperature at ≤−10° C., and the mixture was stirred at ≤−10° C. When the residual amount of ER-076349 was <3% or the generation of corresponding bis-tosylate was more than 4%, the reaction mixture was quenched by the addition of water (1.0 kg). The mixture was warmed up, and then isopropyl alcohol (IPA) (20.5 kg) and ammonium hydroxide ($NH_4OH$; 25.7 kg) were added consecutively at 10-30° C. Upon complete consumption of the epoxide (target≤0.85%; add extra $NH_4OH$ if necessary), the reaction mixture was concentrated in vacuo at <30° C. To the residue, dichloromethane (20.7 kg) and a sufficient amount of buffer solution of $NaHCO_3$/$Na_2CO_3$/water (9/9/182 w/w/w; not more than 5.166 kg) were added and extracted. The organic layer was separated, and the aqueous layer was extracted with dichloromethane (8.6 kg). The organic layer was separated and combined with the first extract. The combined organic layers were concentrated in vacuo at <30° C. The concentrate was diluted with acetonitrile (4.0 kg) and then loaded onto silica gel column which was preequilibrated with acetonitrile (200 L). The column was eluted sequentially with: (1) acetonitrile (100 L), (2) 90.0/7.5/2.5 v/v/v acetonitrile/water/200 mM aqueous $NH_4OAc$ (152.4 L), (3) 85.8/11.7/2.5 v/v/v acetonitrile/water/200 mM aqueous $NH_4OAc$ (152.4 L), (4) 83.5/14.0/2.5 v/v/v acetonitrile/water/200 mM aqueous $NH_4OAc$ (152.6 L), and (5) 80.0/17.6/2.4 v/v/v acetonitrile/water/200 mM aqueous $NH_4OAc$ (>100.2 L). Desired fractions were combined and concentrated in vacuo at ≤40° C. while maintaining the internal pH at 5.5-9.0 by adding $NH_4OH$. To the residue, dichloromethane (13.9 kg) and a sufficient amount of buffer solution of $NaHCO_3$/$Na_2CO_3$/water (9/9/182 w/w/w; not more than 15.51 kg) were added and extracted. The organic layer was separated, and the aqueous layer was extracted with dichloromethane (8.7 kg). The organic layer was separated and combined with the first extract. The combined organic layers were concentrated in vacuo at <30° C. The residue was dissolved in 75% v/v anhydrous dichloromethane in n-pentane (6.12 kg) and filtered. The filtrate was concentrated in vacuo at <30° C., diluted with acetonitrile (2.1 kg), and concentrated in vacuo at 35° C. to give eribulin (75-95% yield).

Methods C3+D1

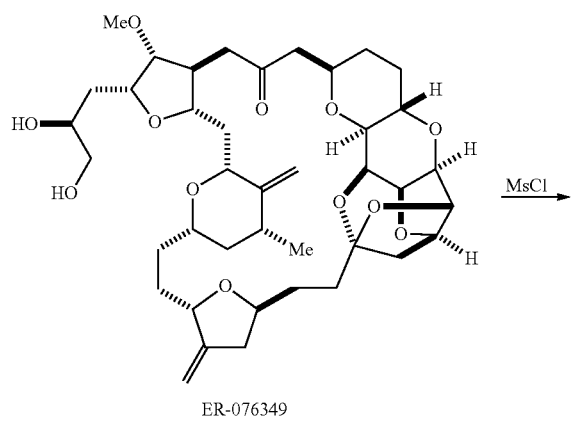

ER-076349

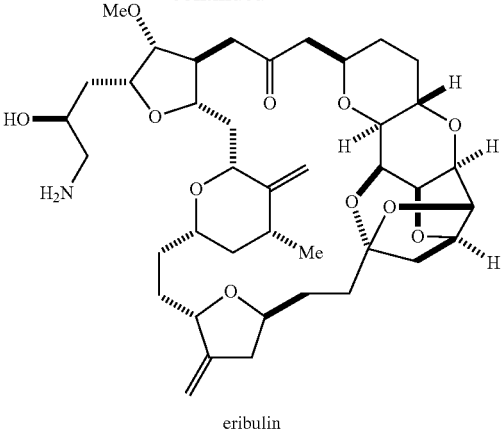

eribulin

MsCl (0.3 M in $CH_2Cl_2$, 98 µL, 0.030 mmol) was added dropwise over 40 min to a mixture of 2,4,6-collidine (7 µL, 0.054 mmol), ER-076349 (20.8 mg, 0.028 mmol), and $CH_2Cl_2$ (1 mL) at 0° C. After 76 h at 4° C., the reaction was quenched with a 1:4 mixture of saturated aqueous $NaHCO_3$-brine and extracted with $CH_2Cl_2$ (4×). The combined extracts were dried over $Na_2SO_4$ and concentrated. The crude product was dissolved in toluene (3 mL), concentrated, and purified by preparative TLC (1.5% MeOH-EtOAc) to afford mesylate B-2294 (21.4 mg, 95%). Tetra-n-butylammonium azide (0.2 M in dimethylformamide, 0.5 mL, 0.10 mmol) was added to a solution of mesylate B-2294 (21.4 mg, 0.026 mmol) in dimethylformamide (2 mL) at room temperature and warmed to 83° C. After stirring at 83° C. for 3.5 h, the reaction mixture was cooled to room temperature, diluted with toluene, concentrated and purified by preparative TLC (80% ethyl acetate-hexanes) to furnish B-1922 (18 mg, 92%). $Me_3P$ (1 M in tetrahydrofuran) and $H_2O$ (0.8 mL) were sequentially added to a solution of azide B-1922 (24.6 mg, 0.032 mmol) in THF (3.2 mL) at room temperature. The mixture was stirred for 22 h, diluted with toluene, concentrated and purified by flash chromatography [step gradient, 10% MeOH-EtOAc followed by MeOH-EtOAc-30% aqueous $NH_4OH$ (9:86:5)] to provide the desired primary amine (23.3 mg), which by $^1$H-NMR contained ~1% trimethylphosphine oxide. Lyophilization from benzene and standing under high vacuum for 2 d furnished eribulin (20.3 mg, 87%).

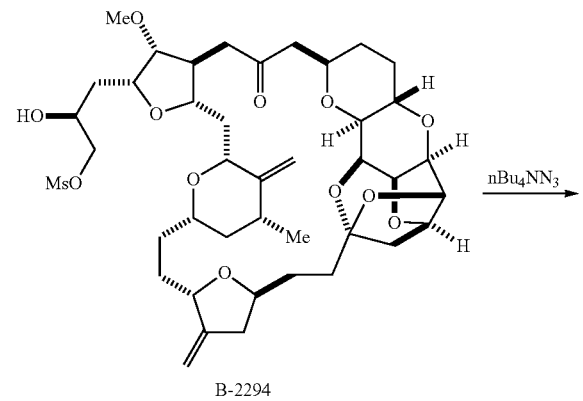

B-2294

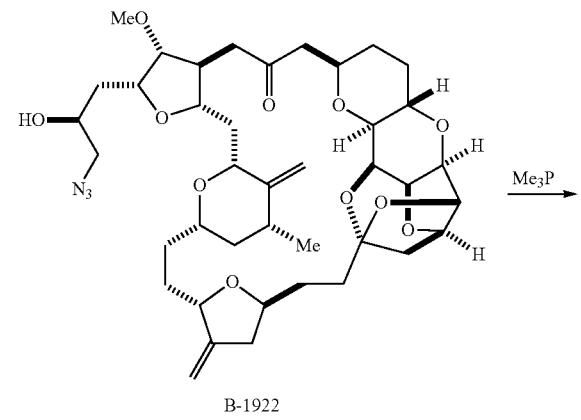

B-1922

Methods C4+D2

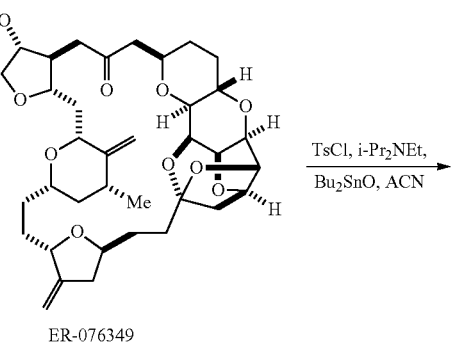

ER-076349

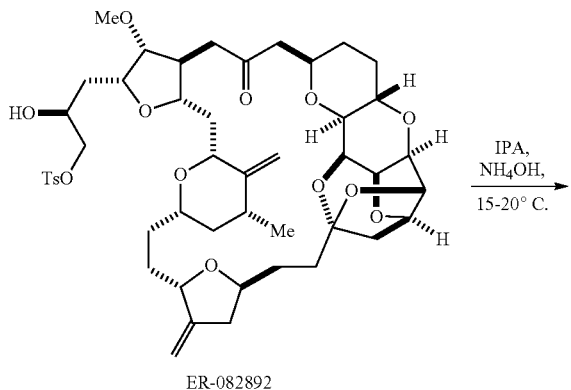

ER-082892

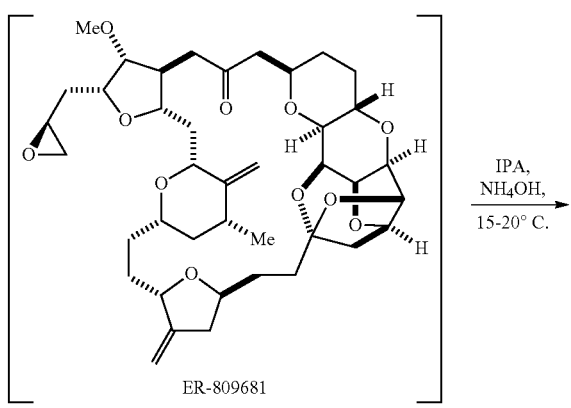

ER-809681

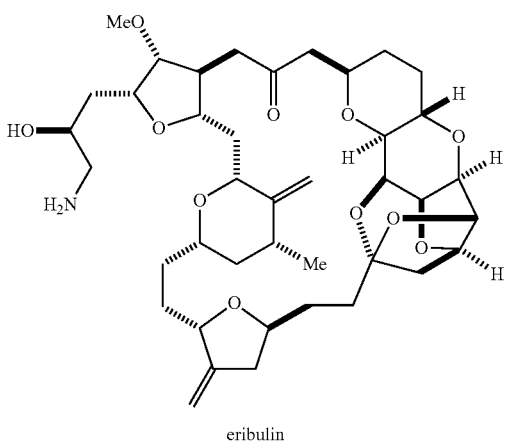

eribulin

The diol ER-076349 (58.3 g) was dissolved in acetonitrile (935 mL). A suspension of dibutyltin oxide (0.99 g) and N,N-diisopropylethylamine (28.5 mL) in acetonitrile (117 mL) were added. A solution of TsCl (30.5 g) in acetonitrile (117 mL) was added to the reaction mixture at a rate to maintain the reaction temperature at 26° C. to 28° C., and the mixture was stirred at 26° C. to 28° C. The reaction was monitored by HPLC for consumption of ER-076349. After the residual level of ER-076349 reached below 3% and reaction time passed over 27 hours, isopropyl alcohol (IPA) (4.58 kg) and ammonium hydroxide (5.82 kg) were added consecutively at 15° C. to 20° C. The mixture was stirred at 15° C. to 20° C. for 66 hours, and the reaction was monitored by HPLC for a consumption of reaction intermediate ER-809681. After the residual level of ER-809681 reached 0.85% or less, the reaction mixture was concentrated in vacuo at 29° C. or below. To the residue, dichloromethane (4.64 kg) and a sufficient amount of buffer solution of $NaHCO_3/Na_2CO_3$/water (9/9/182 w/w/w) (530 mL) were added and extracted. The organic layer was separated, and the aqueous layer was extracted with dichloromethane (1.94 kg). The organic layer was separated, and combined with the first extract. The combined organic layers were concentrated in vacuo at 25° C. or below. The concentrate was diluted with acetonitrile (1.17 L), and then loaded onto silica gel column (5.511 kg) which was pre-equilibrated with acetonitrile (more than 55.1 L). The column was eluted sequentially with acetonitrile (29.6 L), 90.0/7.5/2.5 v/v/v acetonitrile/water/200 mM aqueous $NH_4OAc$ (46.2 L), 85.8/11.7/2.5 v/v/v acetonitrile/water/200 mM aqueous $NH_4OAc$ (45.8 L), 83.5/14.0/2.5 v/v/v acetonitrile/water/200 mM aqueous $NH_4OAc$ (46.5 L), 80.0/17.6/2.4 v/v/v acetonitrile/water/200 mM aqueous $NH_4OAc$ (29.8 L) to remove the unreacted intermediates and the reaction impurities. Desired fractions were combined and concentrated in vacuo at 36° C. or below while maintaining the internal pH at 5.5 to 9.0 by adding ammonium hydroxide. To the residue, dichloromethane (3.98 kg) and a sufficient amount of buffer solution of $NaHCO_3/Na_2CO_3$/water (9/9/182 w/w/w) (2.02 kg) were added and extracted. The organic layer was separated, and the aqueous layer was extracted with dichloromethane (2.48 kg). The organic layer was separated and combined with the first extract. The combined organic layers were concentrated in vacuo at 24° C. or below. The residue was dissolved in 75% v/v anhydrous dichloromethane in n-pentane (1.03 L) and filtered. The filtrate was concentrated in vacuo at 25° C. or below to give eribulin. The residue was diluted with acetonitrile (392 mL) and dichloromethane (69 mL) to give eribulin acetonitrile/dichloromethane solution (assay 49.11 g, corrected yield 85.3%). The solution was concentrated in vacuo at 29° C. or below and used for the next stage.

Salification of Eribulin
Salification to Eribulin Mesylate:

eribulin mesylate: (2R,3R,3aS,7R,8aS,9S,10aR,11S, 12R,13aR,13bS,15S,18S,21S,24S,26R,28R,29aS)-2-[(2S)-3-Amino-2-hydroxypropyl]-3-methoxy-26-methyl-20,27-dimethylidenehexacosahydro-11,15:18,21:24,28-triepoxy-7,9-ethano-12,15-methano-9H,15H-furo[3,2-i]furo[2',3':5,6]pyrano[4,3-b][1,4]dioxacyclopentacosin-5(4H)-one methanesulfonate

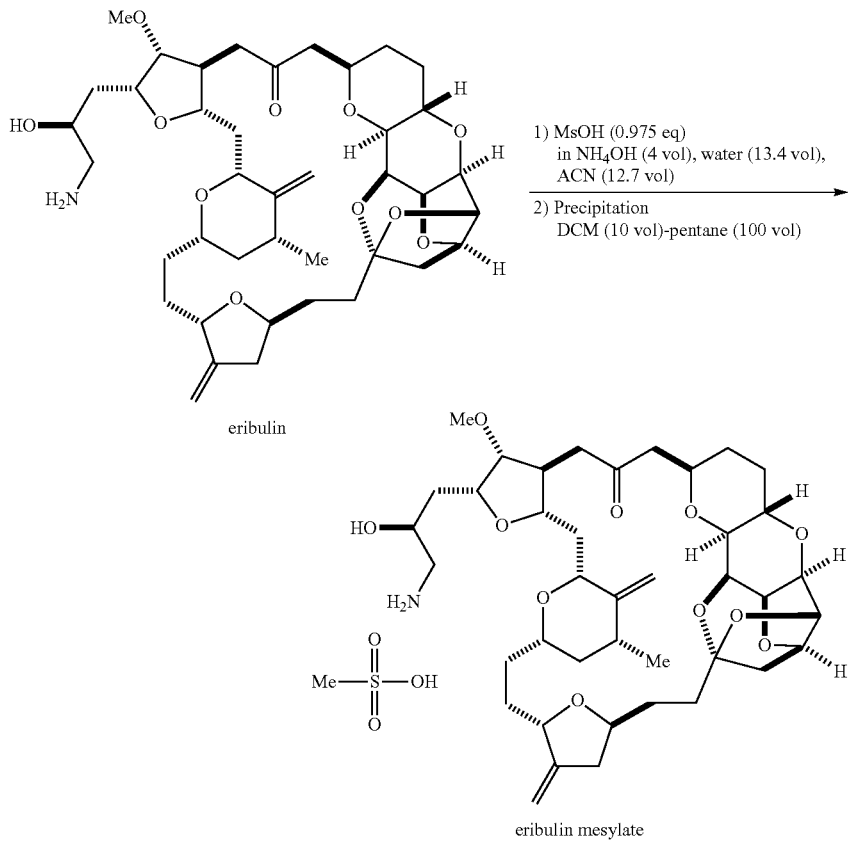

ER-086526-00 (46.68 g) was dissolved in acetonitrile (591 mL) and water (31 mL) and treated with a solution of methanesulfonic acid (MsOH, 4.09 mL) and NH$_4$OH (187 mL) in acetonitrile (624 mL). The mixture was concentrated in vacuo at 24° C. or below and azeotroped repeatedly with anhydrous acetonitrile (234 mL) in vacuo at 24° C. or below to remove water. The residue was dissolved in 75% v/v anhydrous dichloromethane in n-pentane (1.10 L) and filtered. The filtrate was concentrated in vacuo at 24° C. or below. The residue was dissolved in 50% v/v anhydrous dichloromethane in n-pentane (1.16 L), and the solution was transferred through a filter to anhydrous pentane (3.26 kg) in the separate reactor. The resulting precipitate was stirred for 29 hours. The precipitates were filtered, washed with n-pentane (2.92 kg), and dried under nitrogen flow in vacuo until the residual solvent levels reached the target numbers: n-pentane≤25000 ppm; 2-methylbutane≤1000 ppm; 2,2-dimethylbutane≤1000 ppm; and cyclopentane≤1000 ppm. After drying, the precipitates were mixed in vacuo to give eribulin mesylate (gross 45.95 g, corrected yield 83.8%). The drug substance was filled in a polytetrafluoroethylene (PTFE) bottle. The PTFE bottle was packed in an aluminum laminate bag.

Other Embodiments

Various modifications and variations of the described methods of the invention will be apparent to those skilled in the art without departing from the scope and spirit of the invention. Although the invention has been described in connection with certain embodiments, it should be understood that the invention as claimed should not be unduly limited to such embodiments. Indeed, various modifications of the described modes for carrying out the invention that are obvious to those skilled in the relevant art are intended to be within the scope of the invention.

What is claimed is:

1. A method of preparing an intermediate in the synthesis of eribulin, said method comprising reacting a compound having formula (I):

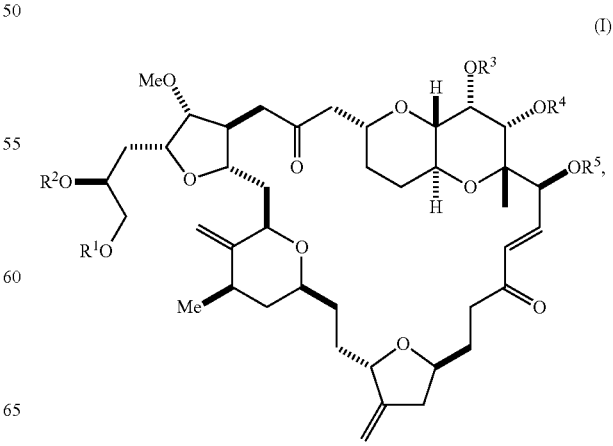

wherein each of $R^1$, $R^2$, $R^3$, $R^4$, and $R^5$ is independently a silyl group, with a fluoride source in a solvent comprising an amide to produce the intermediate ER-811475:

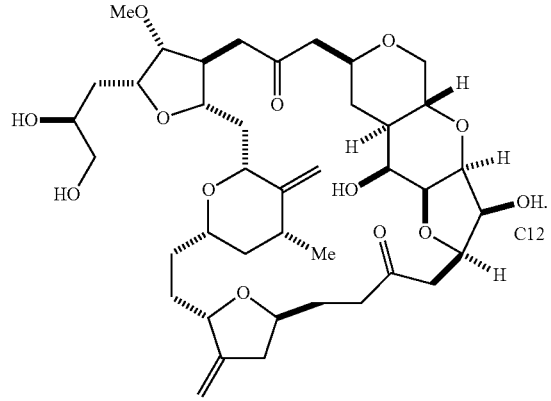

ER-811475 wherein the amide is an N,N C1-C6 dialkyl C1-C6 alkyl amide or N C1-C6 alkyl C2-C6 lactam.

2. The method of claim 1, wherein the intermediate ER-811475 is produced in a mixture with an intermediate ER-811474:

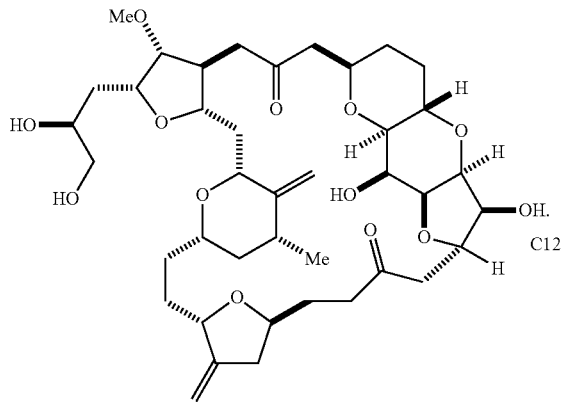

ER-811474

3. The method of claim 2, further comprising adding a mixture of acetonitrile and water.

4. The method of claim 1, wherein each of $R^1$, $R^2$, $R^3$, $R^4$, and $R^5$ is t-butyldimethylsilyl.

5. The method of claim 1, wherein the fluoride source is tetrabutylammonium fluoride.

6. The method of claim 1, wherein the solvent further comprises tetrahydrofuran.

7. The method of claim 1, wherein the amide is N,N-dimethylacetamide, N,N-dimethylformamide, N-methyl 2-pyrrolidone, N,N-diethylacetamide, or N,N-dimethylpropionamide.

8. A method of producing eribulin, said method comprising the steps of:

a) producing an intermediate ER-811475:

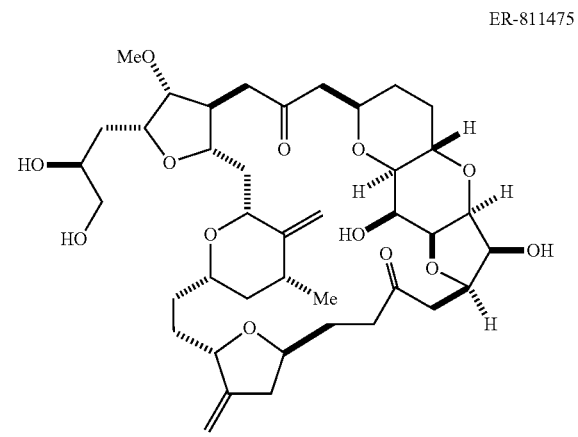

ER-811475 by reacting a compound having formula (I):

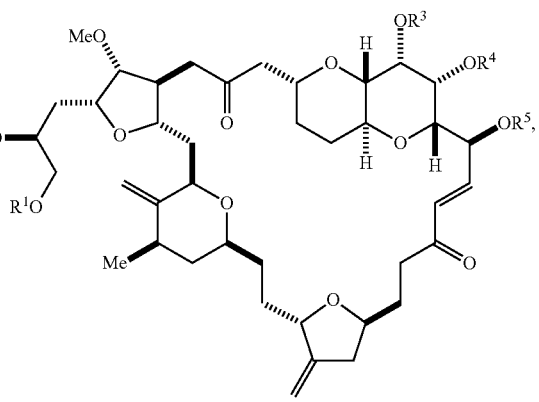

(I)

wherein each of $R^1$, $R^2$, $R^3$, $R^4$, and $R^5$ is independently a silyl group, with a fluoride source in a solvent comprising an amide wherein the amide is an N,N C1-C6 dialkl C1-C6 alkyl amide or N C1-C6 alkyl C2-C6 lactam;

b) ketalizing intermediate ER-811475 to produce the intermediate ER-076349:

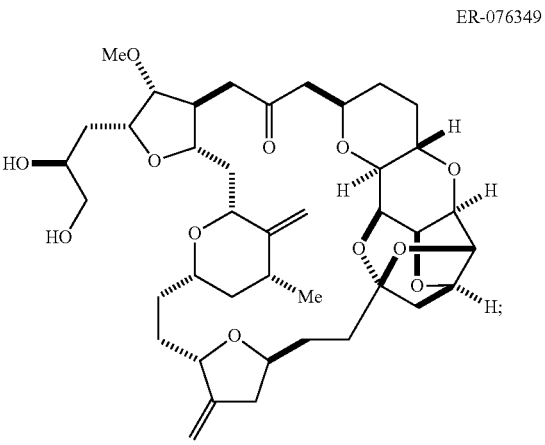

ER-076349 c) aminating ER-076349 to produce eribulin:

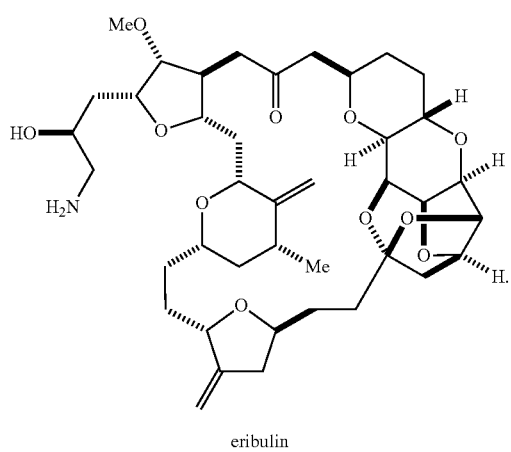

eribulin

9. The method of claim 8, further comprising salifying eribulin to produce a pharmaceutically acceptable salt of eribulin.

10. The method of claim 9, wherein said salt is the mesylate salt.

11. The method of claim 8, wherein ER-076349 is produced by reacting ER-811475 with a conjugate acid of imidazole.

12. The method of claim 8, wherein step c) comprises converting ER-076349 to ER-082892:

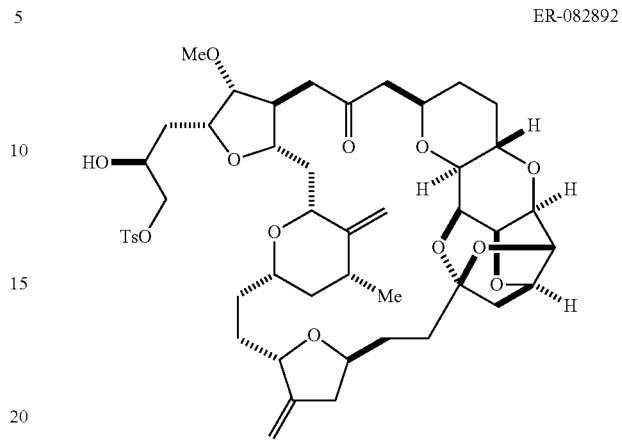

by reacting ER-076349 with a sulfonylating reagent in the presence of a metal catalyst.

* * * * *